(12) United States Patent
Kim et al.

(10) Patent No.: US 7,494,650 B2
(45) Date of Patent: *Feb. 24, 2009

(54) MONOCLONAL ANTIBODIES TO HEPATOCYTE GROWTH FACTOR

(75) Inventors: Kyung Jin Kim, Cupertino, CA (US); Yi-Chi Su, San Francisco, CA (US)

(73) Assignee: Galaxy Biotech, LLC, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/710,009

(22) Filed: Feb. 23, 2007

(65) Prior Publication Data

US 2007/0160613 A1 Jul. 12, 2007

Related U.S. Application Data

(63) Continuation of application No. 10/917,915, filed on Aug. 13, 2004, now Pat. No. 7,220,410, which is a continuation-in-part of application No. 10/825,060, filed on Apr. 15, 2004, now abandoned.

(60) Provisional application No. 60/464,061, filed on Apr. 18, 2003.

(51) Int. Cl.
A61K 39/395 (2006.01)
C12P 21/08 (2006.01)

(52) U.S. Cl. .............. 424/141.1; 424/141.2; 530/388.1; 530/388.15

(58) Field of Classification Search ........................ None
See application file for complete search history.

(56) References Cited

U.S. PATENT DOCUMENTS

| | | | |
|---|---|---|---|
| 5,004,805 A | 4/1991 | Gohda et al. | |
| 5,646,036 A | 7/1997 | Schwall et al. | |
| 5,686,292 A | 11/1997 | Schwall et al. | |
| 5,707,624 A | 1/1998 | Nickoloff et al. | |
| 5,997,868 A | 12/1999 | Goldberg et al. | |
| 6,099,841 A | 8/2000 | Hillan et al. | |
| 6,207,152 B1 | 3/2001 | Schwall et al. | |
| 6,214,344 B1 | 4/2001 | Schwall et al. | |
| 6,432,406 B1 | 8/2002 | Goldberg et al. | |
| 6,468,529 B1 | 10/2002 | Schwall et al. | |
| 7,220,410 B2 | 5/2007 | Kim et al. | |
| 2004/0110685 A1 | 6/2004 | Brandt et al. | |
| 2004/0208876 A1 | 10/2004 | Kim | |
| 2007/0036797 A1 | 2/2007 | Kim | |
| 2007/0160613 A1 | 7/2007 | Kim | |

FOREIGN PATENT DOCUMENTS

| WO | WO91/16928 A1 * | 11/1991 |
|---|---|---|
| WO | WO 01/34650 A1 | 5/2001 |
| WO | WO 03/057155 A2 | 7/2003 |
| WO | WO 2005/001486 A1 | 1/2005 |
| WO | WO 2005/007193 A2 | 1/2005 |
| WO | WO 2005/017107 A2 | 2/2005 |
| WO | WO 2005/044848 A1 | 5/2005 |
| WO | WO 2005/107800 A1 | 11/2005 |
| WO | WO 2006/130773 A2 | 12/2006 |

OTHER PUBLICATIONS

U.S. Appl. No. 60/788,243, filed Apr. 1, 2006, Kim.
U.S. Appl. No. 60/751,092, filed Dec. 15, 2005, Kim.
U.S. Appl. No. 60/687,118, filed Jun. 2, 2005, Kim.
U.S. Appl. No. 60/464,061, filed Apr. 18, 2003, Kim.
U.S. Appl. No. 11/818,305, filed Jun. 13, 2007, Kim et al.
U.S. Appl. No. 11/731,774, filed Mar. 29, 2007, Kim.
Abounader et al., "Reversion of Human Glioblastoma Malignancy by U1 Small Nuclear RNA/Ribozyme Targeting of Scatter Factor/Hepatocyte Growth Factor and c-met Expression," *J Natl Cancer Inst*, 91:1548-1556 (1999).
Advisory Action mailed Dec. 19, 2006 for U.S. Appl. No. 10/917,915.
Advisory Action mailed Oct. 30, 2006 for U.S. Appl. No. 10/917,915.
Anti-Human Hepatocyte Growth Factor (HGF) Developed in Goat, Affinity Isolated Antibody, product No. H7157, brochure for Sigma®.
Birchmeier et al., "Met, Metastasis, Motility and More," *Nature Reviews*, 4:915-925 (2003).
Brockmann et al., "Inhibition of Intracerebral Glioblastoma Growth by Local Treatment with the Scatter Factor/Hepatocyte Growth Factor-Antagonist NK4," *Clinical Cancer Research*, 9:4578-4585 (2003).
Burgess et al., "Fully Human Monoclonal Antibodies to Hepatocyte Growth Facto with Therapeutic Potential against Hepocyte Growth Factor/c-Met-Dependent human Tumors," *Cancer Res.*, 66(3):1721-1729 (2006).
Burr et al., "Anti-Hepatocyte Growth Factor Antibody Inhibits Hepatocyte Proliferation During Liver Regeneration," *Journal of Pathology*, 185:298-302 (1998).
Cao et al., "Neutralizing monoclonal antibodies to hepatocyte growth factor / scatter factor HGF / SF) display antitumor activity in animal models," *PNAS*, 98(13):7443-7448 (2001).
Danilkovitch-Miagkova et al., "Dysregulation of Met receptor tyrosine kinase activity in invasive tumors," *J. Clinical Investigation*, 109(7):863-867 (2002).
Date et al., "Inhibition of tumor growth and invasion by a four kringle antagonist HGF / NK4) for hepatocyte growth factor," *Oncogene*, 17:3045-3054 (1998).
Davies et al., "The HGF/SF Antagonist NK4 Reversed Fibroblast- and HGF-Induced prostate Tumor Growth and Angiogenesis in Vivo," *Int. J. Cancer*, 106:348-354 (2003).
Di Nicola et al., "Human bone marrow stromal cells suppress T-lymphocyte proliferation induced by cellular or nonspecific mitogenic stimuli," *Blood*, 99(10):3838-3843 (2002).

(Continued)

*Primary Examiner*—Ruixiang Li
(74) *Attorney, Agent, or Firm*—Townsend and Townsend and Crew LLP

(57) ABSTRACT

The present invention is directed toward a neutralizing monoclonal antibody to hepatocyte growth factor, a pharmaceutical composition comprising same, and methods of treatment comprising administering such a pharmaceutical composition to a patient.

18 Claims, 12 Drawing Sheets

OTHER PUBLICATIONS

Examiner Interview Summary mailed Oct. 26, 2006 for U.S. Appl. No. 10/917,915.

Hayashi et al., "Autocrine-Paracrine Effects of Overexpression of Heptocyte Growth Factor Gene on Growth of Endothelial Cells," *Biochem Biophys. Res. Comm.*, 220:539-545 (1996).

International Preliminary Report on Patentability with Written Opinion for PCT/US04/26565 mailed Jan. 7, 2005.

International Search Report for PCT/US04/26565 mailed Jan. 7, 2005.

Kermorgant et al., "Hepatocyte growth factor induces colonic cancer cell invasiveness via enhanced motility and protease overproduction. Evidence for PI3 kinase involvement," *Carcinogenesis*, 22(7):1035-1042 (2001).

Kim et al., "Systemic Anti-Hepatocyte Growth Factor Monoclonal Antibody Therapy Induces the Regression of Intracranial Glioma Xenografts," *Clin. Cancer Res.*, 12(4):1292-1298 (2006).

Koochekpour et al., "Met and Hepatocyte Growth Factor/Scatter Factor Expression in Human Gliomas(1)," *Cancer Research*, 57:5391-5398 (1997).

Kuba et al., "HGF/NK4, a Four-Kringle Antagonist of Hepatocyte Growth Factor, Is an Angiogenesis Inhibitor that Suppresses Tumor Growth and Metastasis in Mice," *Cancer Research*, 60:6737-6743 (2000).

Maulik et al., "Role of the hepatocyte growth factor receptor, c-Met, in oncogenesis and potential for therapeutic inhibition," *Cytokine & Growth Factor Reviews*, 13:41-59 (2002).

Michieli et al., "Targeting the tumor and its microenvironment by a dual-function decoy Met receptor," *Cancer Cell*, 6:61-73 (2004).

Monoclonal Anti-human HGF Antibody, brochure dated Jun. 3, 2002 by R & D Systems downloaded from WWW.rndsystems.com/pdf/MAF284.pdf.

Nishimura et al., "Prostate Stromal Cell-Derived Hepatocyte Growth Factor Induces Invasion of Prostate Cancer Cell Line DUI 45 Through Tumor-Stromal Interaction," *Prostate*, 41:145-153 (1999).

Office Action mailed Jan. 10, 2006 for U.S. Appl. No. 10/917,915.
Office Action mailed Mar. 14, 2006 for U.S. Appl. No. 10/917,915.
Office Action mailed Aug. 11, 2006 for U.S. Appl. No. 10/917,915.

Prat et al., "Agonistic monoclonal antibodies against the Met receptor dissect the biological responses to HGF," *Journal of Cell Science*, 111:237-247 (1998).

Principal Investigator: Jin K. Kim, Abstract of Grant No. 2R44CA101283-02, "Novel Monoclonal Antibody Therapy for Cancer," pp. 1-2 from CRISP database, published *ca*. Aug. 2005.

Principal Investigator: Jin K. Kim, Abstract of Grant No. 1R43CA101283-01A1, "Novel Monoclonal Antibody Therapy for Cancer," pp. 1-2 from CRISP database, published *ca*. Apr. 2004.

Principal Investigator: John L. Lattera, Abstract of Grant No. 2R01NS032148-04, "Biochemistry of Brain Tumor Microvessel Development," pp. 1-2 printed from CRISP, published *ca*. (1998).

Response dated Jan. 18, 2007 to Final Office Action mailed Aug. 11, 2006 for U.S. Appl. No. 10/917,915.

Response dated Nov. 15, 2006 to Final Office Action mailed Aug. 11, 2006 for U.S. Appl. No. 10/917,915.

Response dated Apr. 14, 2006 to Office Action mailed Mar. 14, 2006 for U.S. Appl. No. 10/917,915.

Response dated Jan. 27, 2006 to Restriction Requirement mailed Jan. 10, 2006 for U.S. Appl. No. 10/917,915.

Response Draft for Discussion with Examiner Only submitted Oct. 16, 2006 to Final Office Action mailed Aug. 11, 2006 for U.S. Appl. No. 10/917,915.

Schwall et al., "Inhibition of cmet activation by a one-armed antibody," *Proceedings of AACR*, #1424 from vol. 45 (2004).

Supplemental Amendment dated Apr. 25, 2006 for U.S. Appl. No. 10/917,915.

Supplementary Partial European Search Report for European Application No. 04781281 dated Mar. 6, 2007.

Zaccolo et al., "Dimerization of Fab fragments enables ready screening of phage antibodies that affect hepatocyte growth factor/scatter factor activity on target cells," *Eur. J. Immunol.*, 27:618-623 (1997).

\* cited by examiner

MONOCLONAL ANTIBODIES TO HEPATOCYTE GROWTH FACTOR

CROSS-REFERENCES TO RELATED APPLICATIONS

This application is a continuation of Ser. No. 10/917,915 filed Aug. 13, 2004, issued as U.S. Pat. No. 7,220,410, which is a continuation-in-part of U.S. patent application Ser. No. 10/825,060 filed Apr. 15, 2004, now abandoned which claims the benefit of the provisional application U.S. Patent Application No. 60/464,061 filed Apr. 18, 2003, both of which are incorporated by reference in their entirety for all purposes.

FIELD OF THE INVENTION

The present invention relates generally to the combination of monoclonal antibody (mAb) and recombinant DNA technologies for developing novel biologics, and more particularly, for example, to the production of monoclonal antibodies that bind to and neutralize Hepatocyte Growth Factor.

BACKGROUND OF THE INVENTION

Human Hepatocyte Growth Factor (HGF) is a multifunctional heterodimeric polypeptide produced by mesenchymal cells. HGF has been shown to stimulate angiogenesis, morphogenesis and motogenesis, as well as the growth and scattering of various cell types (Bussolino et al., J. Cell. Biol. 119: 629, 1992; Zarnegar and Michalopoulos, J. Cell. Biol. 129: 1177, 1995; Matsumoto et al., Ciba. Found. Symp. 212:198, 1997; Birchmeier and Gherardi, Trends Cell. Biol. 8:404, 1998; Xin et al. Am. J. Pathol. 158:1111, 2001). The pleiotropic activities of HGF are mediated through its receptor, a transmembrane tyrosine kinase encoded by the proto-oncogene cMet. In addition to regulating a variety of normal cellular functions, HGF and its receptor c-Met have been shown to be involved in the initiation, invasion and metastasis of tumors (Jeffers et al., J. Mol. Med. 74:505, 1996; Comoglio and Trusolino, J. Clin. Invest. 109:857, 2002). HGF/cMet are coexpressed, often over-expressed, on various human solid tumors including tumors derived from lung, colon, rectum, stomach, kidney, ovary, skin, multiple myeloma and thyroid tissue (Prat et al., Int. J. Cancer 49:323, 1991; Chan et al., Oncogene 2:593, 1988; Weidner et al., Am. J. Respir. Cell. Mol. Biol. 8:229, 1993; Derksen et al., Blood 99:1405, 2002). HGF acts as an autocrine (Rong et al., Proc. Natl. Acad. Sci. USA 91:4731, 1994; Koochekpour et al., Cancer Res. 57:5391, 1997) and paracrine growth factor (Weidner et al., Am. J. Respir. Cell. Mol. Biol. 8:229, 1993) and anti-apoptotic regulator (Gao et al., J. Biol. Chem. 276:47257, 2001) for these tumors.

HGF is a 102 kDa protein with sequence and structural similarity to plasminogen and other enzymes of blood coagulation (Nakamura et al., Nature 342:440, 1989; Weidner et al., Am. J. Respir. Cell. Mol. Biol. 8:229, 1993, each of which is incorporated herein by reference) (FIG. 1). Human HGF is synthesized as a 728 amino acid precursor (preproHGF), which undergoes intracellular cleavage to an inactive, single chain form (proHGF) (Nakamura et al., Nature 342:440, 1989; Rosen et al., J. Cell. Biol. 127:1783, 1994). Upon extracellular secretion, proHGF is cleaved to yield the biologically active disulfide-linked heterodimeric molecule composed of an α-subunit and β-subunit (Nakamura et al., Nature 342:440, 1989; Naldini et al., EMBO J. 11:4825, 1992). The α-subunit contains 440 residues (69 kDa with glycosylation), consisting of the N-terminal hairpin domain and four kringle domains. The β-subunit contains 234 residues (34 kDa) and has a serine protease-like domain, which lacks proteolytic activity. Cleavage of HGF is required for receptor activation, but not for receptor binding (Hartmann et al., Proc. Natl. Acad. Sci. USA 89:11574, 1992; Lokker et al., J. Biol. Chem. 268:17145, 1992). HGF contains 4 putative N-glycosylation sites, 1 in the α-subunit and 3 in the β-subunit. HGF has 2 unique cell specific binding sites: a high affinity ($Kd=2\times10^{-10}$ M) binding site for the cMet receptor and a low affinity ($Kd=10^{-9}$ M) binding site for heparin sulfate proteoglycans (HSPG), which are present on the cell surface and extracellular matrix (Naldini et al., Oncogene 6:501, 1991; Bardelli et al., J. Biotechnol. 37:109, 1994; Sakata et al., J. Biol. Chem., 272:9457, 1997). NK2 (a protein encompassing the N-terminus and first two kringle domains of the α-subunit) is sufficient for binding to cMet and activation of the signal cascade for motility, however the full length protein is required for the mitogenic response (Weidner et al., Am. J. Respir. Cell. Mol. Biol. 8:229, 1993). HSPG binds to HGF by interacting with the N terminus of HGF (Aoyama, et al., Biochem. 36:10286, 1997; Sakata, et al., J. Biol. Chem. 272:9457, 1997). Postulated roles for the HSPG-HGF interaction include the enhancement of HGF bioavailability, biological activity and oligomerization (Bardelli, et al., J. Biotechnol. 37:109, 1994; Zioncheck et al., J. Biol. Chem. 270: 16871, 1995).

cMet is a member of the class IV protein tyrosine kinase receptor family. The full length cMet gene was cloned and identified as the cMet proto-oncogene (Cooper et al., Nature 311:29, 1984; Park et al., Proc. Natl. Acad. Sci. USA 84:6379, 1987). The cMet receptor is initially synthesized as a single chain, partially glycosylated precursor, $p170^{(MET)}$ (FIG. 1) (Park et al., Proc. Natl. Acad. Sci. USA 84:6379, 1987; Giordano et al., Nature 339:155, 1989; Giordano et al., Oncogene 4:1383, 1989; Bardelli et al., J. Biotechnol. 37:109, 1994). Upon further glycosylation, the protein is proteolytically cleaved into a heterodimeric 190 kDa mature protein (1385 amino acids), consisting of the 50 kDa α-subunit (residues 1-307) and the 145 kDa β-subunit. The cytoplasmic tyrosine kinase domain of the β-subunit is involved in signal transduction.

Several different approaches have been investigated to obtain an antagonistic molecule of the HGF/cMet interaction: truncated HGF proteins such as NK1 (N terminal domain plus kringle domain 1; Lokker et al., J. Biol. Chem. 268:17145, 1993), NK2 (N terminal domain plus kringle domains 1 and 2; Chan et al., Science 254:1382, 1991) and NK4 (N-terminal domain plus four kringle domains; Kuba et al., Cancer Res. 60:6737, 2000), anti-cMet mAbs (Dodge, Master's Thesis, San Francisco State University, 1998) and anti-HGF mAbs (Cao et al., Proc. Natl. Acad. Sci. USA 98:7443, 2001, which is incorporated herein by reference).

NK1 and NK2 can compete effectively with the binding of HGF to its receptor, but have been shown to have partial agonistic activities in vitro (Cioce et al., J. Biol. Chem. 271: 13110, 1996; Schwall et al., J. Cell Biol. 133:709, 1996), rather than purely antagonist activities as desired. More recently, Kuba et al., Cancer Res. 60:6737, 2000, demonstrated that NK4 could partially inhibit the primary growth (FIG. 2) and metastasis of murine lung tumor LLC in a nude mouse model by continuous infusion of NK4. The fact that NK4 had to administered continuously to obtain a partial growth inhibition of primary tumors indicates a potentially short half-life of the NK4 molecule and/or lack of potency. Compared to NK4, the approach of using antibodies will benefit from their favorable pharmacokinetics and the possibility of obtaining antibodies with much higher potency.

As another approach, Dodge (Master's Thesis, San Francisco State University, 1998) generated antagonistic anti-cMet monoclonal antibodies (mAbs). One mAb, 5D5, exhibited strong antagonistic activity in ELISA, but induced a proliferative response of cMet-expressing BAF-3 cells, presumably due to dimerization of the membrane receptors. Prat et al., J. Cell Sci. 111:237, 1998, also reported such agonistic activities of anti-cMet mAbs. Zaccolo et al., Eur. J. Immunol 27:618, 1997, used phage display methods do develop human Fab fragments against mouse and human hepatocyte growth factor. These Fab fragments had no effect on the activity of HGF when used alone. When one of the anti-human HGF Fab fragments was combined with an antibody that bound to the Fab fragment itself, it actually enhanced the activity of HGF in a biological assay.

Cao et al., Proc. Natl. Acad. Sci. USA 98:7443, 2001, demonstrated that the administration of a cocktail of three anti-HGF mAbs, which were selected based upon their ability to inhibit the scattering activity of HGF in vitro, were able to inhibit the growth of human tumors in the xenograft nude mouse model (FIG. 3). They postulated that three mAbs recognizing three different binding sites on HGF were required to inhibit the bioactivities of HGF in vivo: two mAbs inhibited the binding of HGF to cMet and one mAb inhibited the binding of HGF to heparin. However, it is impractical for commercial and regulatory reasons to develop a drug combining three novel mAbs, e.g., because some clinical activity of each antibody would need to be demonstrated independently.

Thus, there is a need for a single monoclonal antibody that blocks biological activity of HGF in vitro and in vivo. The present invention fulfills this and other needs.

BRIEF SUMMARY OF THE INVENTION

In one embodiment, the invention provides a neutralizing mAb to human Hepatocyte Growth Factor (HGF). The mAb inhibits at least one, and preferably several or all biological activities of HGF including binding to its receptor cMet, inducing scattering of cells such as Madin-Darby canine kidney cells, inducing proliferation of 4MBr-5 monkey epithelial cells and/or hepatocytes and/or HUVEC, and inducing angiogenesis. The Anti-HGF mAb can inhibit such an activity when used as a single agent. A preferred anti-HGF mAb inhibits, most preferably completely inhibits, growth of a human tumor xenograft in a mouse. Preferably, the mAb of the invention is chimeric, humanized, human-like or human. Exemplary antibodies are L2G7 and its chimeric and humanized forms. Cell lines producing such antibodies are also provided. In another embodiment, a pharmaceutical composition comprising a neutralizing anti-HGF antibody, e.g., chimeric or humanized L2G7, is provided. In a third embodiment, the pharmaceutical composition is administered to a patient to treat cancer or other disease.

DETAILED DESCRIPTION OF THE INVENTION

Figure 1:
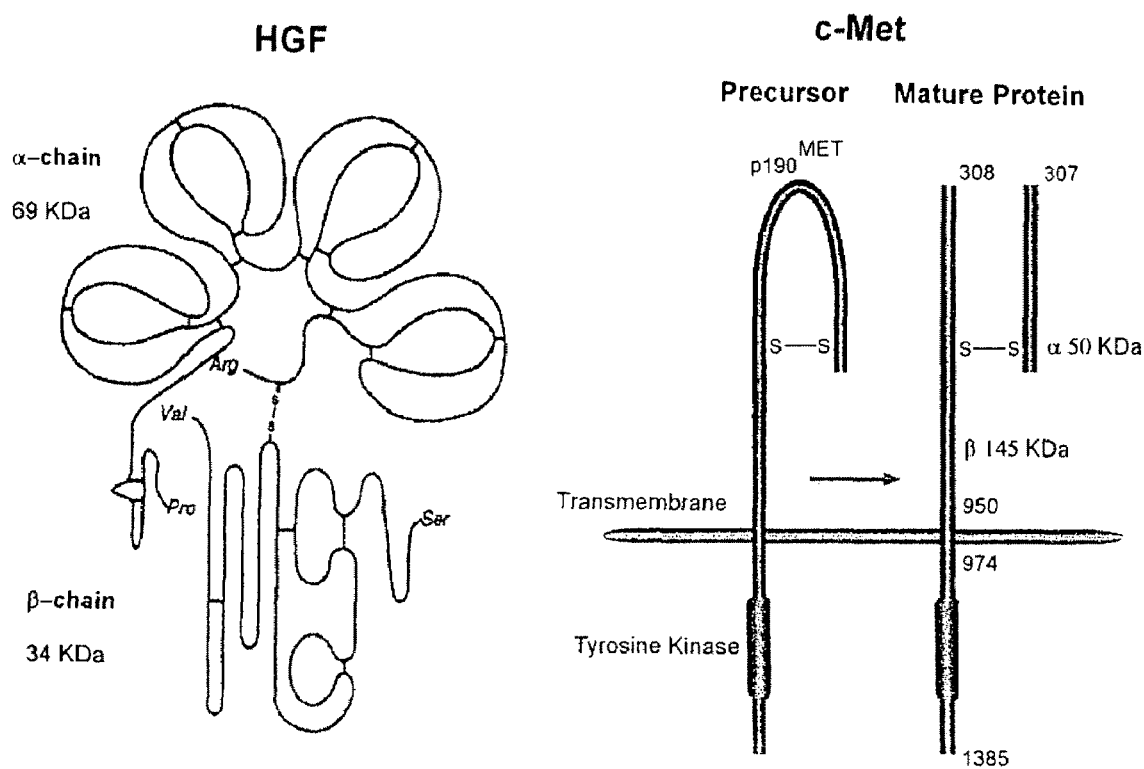
FIG. 1. Schematic models of HGF and cMet.
Figure 2:
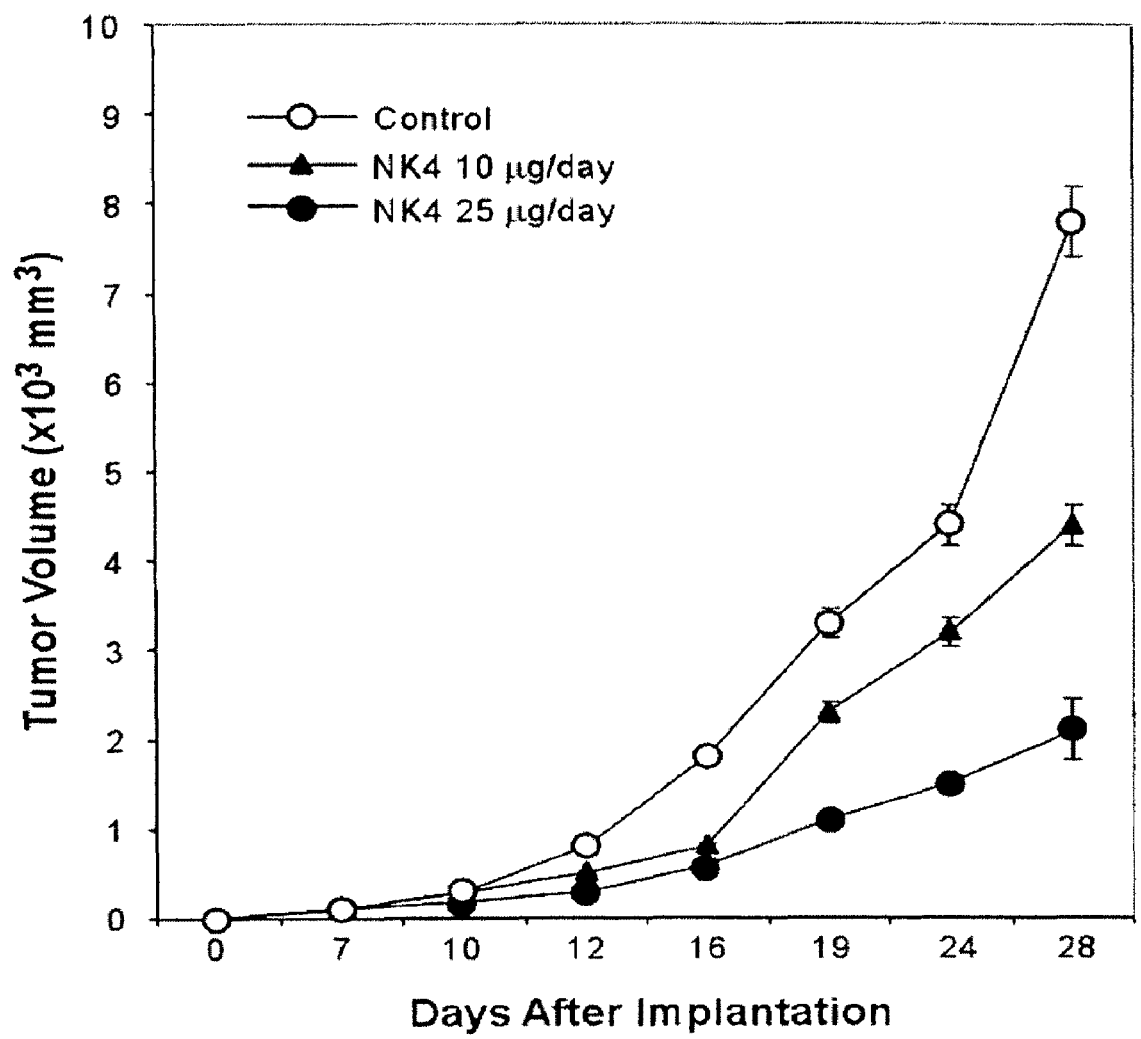
FIG. 2. Graph showing that NK4 partially inhibits the primary growth of murine lung tumor LLC in nude mice (from Kuba et al., Cancer Res. 60:6737, 2000). NK4 was infused continuously for 14 days from 4$^{th}$ day after tumor implantation s.c. in nude mice.
Figure 3:
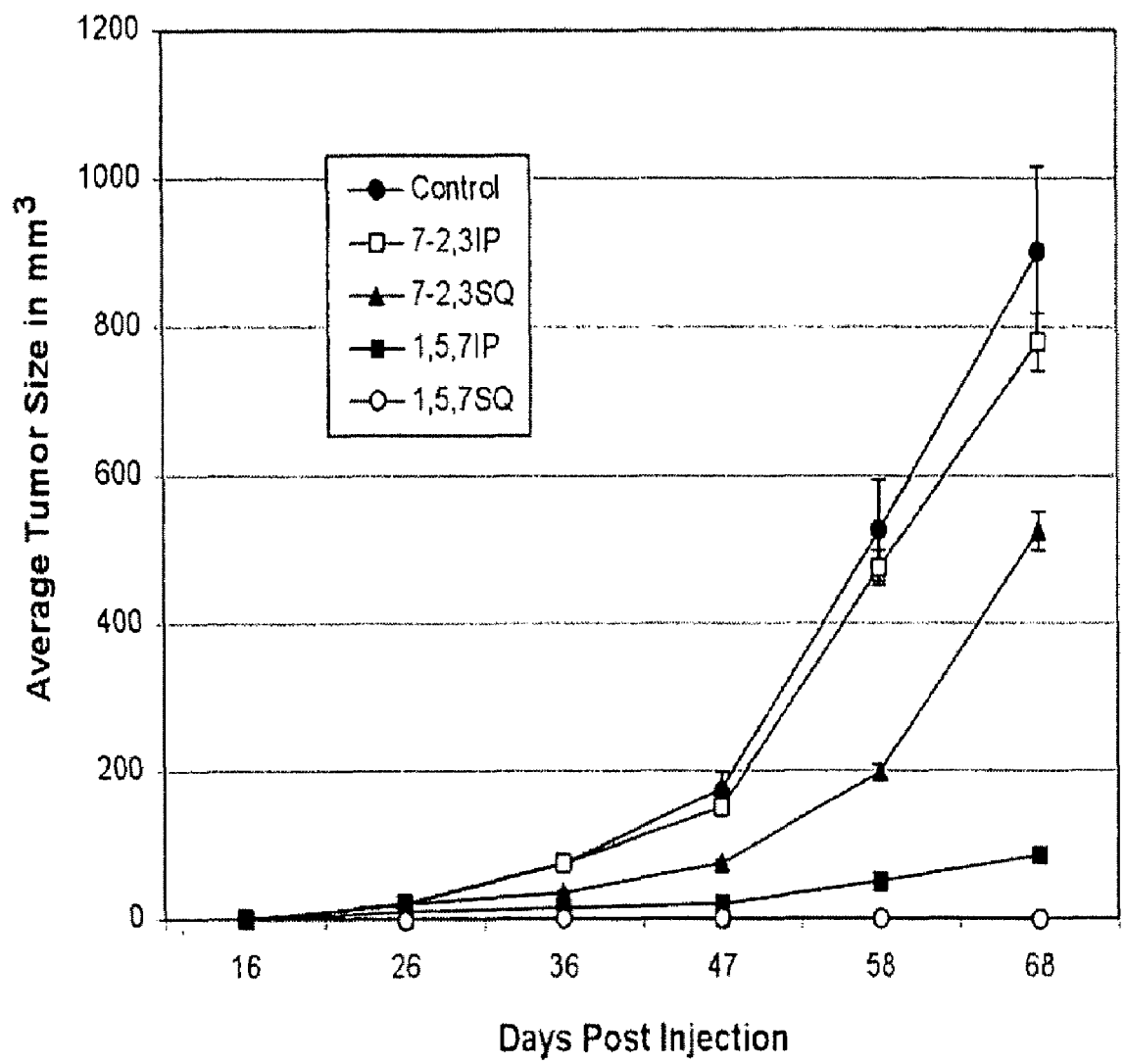
FIG. 3. Graph showing that a cocktail of three anti-HGF mAbs is required to inhibit the growth of human brain tumor U-118 in nude mice (from Cao et al., Proc. Natl. Acad. Sci. USA 98:7443, 2001). U-118 tumor cells were injected s.c. into nude mice. From day 1 anti-HGF mAbs A-1, -5, and -7, or mAbs 7-2 and -3 were administered at 200 μg/injection, twice/wk for 10 wks.

The invention provides neutralizing anti-HGF monoclonal antibodies, pharmaceutical compositions comprising them, and methods of using them for the treatment of disease.

1. Antibodies

Antibodies are very large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions fold up together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-D space to form the actual antibody binding site which locks onto the target antigen. The position and length of the CDRs have been precisely defined. Kabat, E. et al., Sequences of Proteins of Immunological Interest, U.S. Department of Health and Human Services, 1983, 1987. The part of a variable region not contained in the CDRs is called the framework, which forms the environment for the CDRs.

A monoclonal antibody (mAB) is a single molecular species of antibody and therefore does not encompass polyclonal antibodies produced by injecting an animal (such as a rodent, rabbit or goat) with an antigen, and extracting serum from the animal. A humanized antibody is a genetically engineered (monoclonal) antibody in which the CDRs from a mouse antibody ("donor antibody", which can also be rat, hamster or other similar species) are grafted onto a human antibody ("acceptor antibody"). Humanized antibodies can also be made with less than the complete CDRs from a mouse antibody (e.g., Pascalis et al., J. Immunol. 169:3076, 2002). Thus, a humanized antibody is an antibody having CDRs from a donor antibody and variable region framework and constant regions from a human antibody. Thus, typically a humanized antibody comprises (i) a light chain comprising three CDRs from a mouse antibody, e.g., L2G7, a variable region framework from a human antibody, and a human constant region, and (ii) a heavy chain comprising three CDRs from a mouse antibody, e.g., L2G7, a variable region framework from a human antibody and a human constant region. In addition, in order to retain high binding affinity, at least one of two additional structural elements can be employed. See, U.S. Pat. Nos. 5,530,101 and 5,585,089, each of which is incorporated herein by reference, which provide detailed instructions for construction of humanized antibodies.

In the first structural element, the framework of the heavy chain variable region of the humanized antibody is chosen to have maximal sequence identity (between 65% and 95%) with the framework of the heavy chain variable region of the donor antibody, by suitably selecting the acceptor antibody from among the many known human antibodies. Sequence identity is determined when antibody sequences being compared are aligned according to the Kabat numbering convention. In the second structural element, in constructing the humanized antibody, selected amino acids in the framework of the human acceptor antibody (outside the CDRs) are replaced with corresponding amino acids from the donor antibody, in accordance with specified rules. Specifically, the amino acids to be replaced in the framework are chosen on the basis of their ability to interact with the CDRs. For example, the replaced amino acids can be adjacent to a CDR in the donor antibody sequence or within 4-6 angstroms of a CDR in the humanized antibody as measured in 3-dimensional space.

A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

As used herein, the term "human-like" antibody refers to a Mab in which a substantial portion of the amino acid sequence of one or both chains (e.g., about 50% or more) originates from human immunoglobulin genes. Hence, human-like antibodies encompass but are not limited to chimeric, humanized and human antibodies. As used herein, a "reduced-immunogenicity" antibody is one expected to have significantly less immunogenicity than a mouse antibody when administered to human patients. Such antibodies encompass chimeric, humanized and human antibodies as well as antibodies made by replacing specific amino acids in mouse antibodies that may contibute to B- or T-cell epitopes, for example exposed residues (Padlan, Mol. Immunol. 28:489, 1991). As used herein, a "genetically engineered" antibody is one for which the genes have been constructed or put in an unnatural environment (e.g., human genes in a mouse or on a bacteriophage) with the help of recombinant DNA techniques, and would therefore, e.g., not encompass a mouse mAb made with conventional hybridoma technology.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 50% but preferably 75%, 90% or even 99% as measured in a competitive binding assay compared to a control lacking the competing antibody (see, e.g., Junghans et al., Cancer Res. 50:1495, 1990, which is incorporated herein by reference). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

2. Neutralizing Anti-HGF Antibodies

A monoclonal antibody (mAb) that binds HGF (i.e., an anti-HGF mAb) is said to neutralize HGF, or be neutralizing, if the binding partially or completely inhibits one or more biological activities of HGF (i.e., when the mAb is used as a single agent). Among the biological properties of HGF that a neutralizing antibody may inhibit are the ability of HGF to bind to its cMet receptor, to cause the scattering of certain cell lines such as Madin-Darby canine kidney (MDCK) cells; to stimulate proliferation of (i.e., be mitogenic for) certain cells including hepatocytes, 4MBr-5 monkey epithelial cells, and various human tumor cells; or to stimulate angiogenesis, for example as measured by stimulation of human vascular endothelial cell (HUVEC) proliferation or tube formation or by induction of blood vessels when applied to the chick embryo chorioallantoic membrane (CAM). Antibodies of the invention preferably bind to human HGF, i.e., to the protein encoded by the GenBank sequence with Accession number D90334 (incorporated by reference).

A neutralizing mAb of the invention at a concentration of, e.g., 0.01, 0.1, 0.5, 1, 2, 5, 10, 20 or 50 µg/ml will inhibit a biological function of HGF (e.g., stimulation of proliferation or scattering) by about at least 50% but preferably 75%, more preferably by 90% or 95% or even 99%, and most preferably approximately 100% (essentially completely) as assayed by methods described under Examples or known in the art. Inhibition is considered complete if the level of activity is within the margin of error for a negative control lacking HGF. Typically, the extent of inhibition is measured when the amount of HGF used is just sufficient to fully stimulate the biological activity, or is 0.05, 0.1, 0.5, 1, 3 or 10 μg/ml. Preferably, at least 50%, 75%, 90%, or 95% or essentially complete inhibition will be achieved when the molar ratio of antibody to HGF is 0.5×, 1×, 2×, 3×, 5× or 10×. Preferably, the mAb will be neutralizing, i.e., inhibit the biological activity, when used as a single agent, but possible 2 mAbs will be needed together to give inhibition. Most preferably, the mAb will neutralize not just one but several of the biological activities listed above; for purposes herein, an anti-HGF mAb that used as a single agent neutralizes all the biological activities of HGF will be called "fully neutralizing", and such mAbs are most preferable. MAbs of the invention will preferably be specific for HGF, that is they will not bind, or only bind to a much lesser extent (e.g., Ka at least ten-fold less), proteins that are related to HGF such as fibroblast growth factor (FGF) and vascular endothelial growth factor (VEGF). Preferred antibodies lack agonistic activity toward HGF. That is, the antibodies block interaction of HGH with cMet without stimulating cells bearing HGF directly. MAbs of the invention typically have a binding affinity ($K_a$) for HGF of at least $10^7$ $M^{-1}$ but preferably $10^8$ $M^{-1}$ or higher, and most preferably $10^9$ $M^{-1}$ or higher or even $10^{10}$ $M^{-1}$ or higher.

MAbs of the invention include anti-HGF antibodies in their natural tetrameric form (2 light chains and 2 heavy chains) and may be of any of the known isotypes IgG, IgA, IgM, IgD and IgE and their subtypes, i.e., human IgG1, IgG2, IgG3, IgG4 and mouse IgG1, IgG2a, IgG2b, and IgG3. The mAbs of the invention are also meant to include fragments of antibodies such as Fv, Fab and F(ab')$_2$; bifunctional hybrid antibodies (e.g., Lanzavecchia et al., Eur. J. Immunol. 17:105, 1987), single-chain antibodies (Huston et al., Proc. Natl. Acad. Sci. USA 85:5879, 1988; Bird et al., Science 242:423, 1988); and antibodies with altered constant regions (e.g., U.S. Pat. No. 5,624,821). The mAbs may be of animal (e.g., mouse, rat, hamster or chicken) origin, or they may be genetically engineered. Rodent mAbs are made by standard methods well-known in the art, comprising multiple immunization with HGF in appropriate adjuvant i.p., i.v., or into the footpad, followed by extraction of spleen or lymph node cells and fusion with a suitable immortalized cell line, and then selection for hybridomas that produce antibody binding to HGF, e.g., see under Examples. Chimeric and humanized mAbs, made by art-known methods mentioned supra, are preferred embodiments of the invention. Human antibodies made, e.g., by phage display or transgenic mice methods are also preferred (see e.g., Dower et al., McCafferty et al., Winter, Lonberg et al., Kucherlapati, supra). More generally, human-like, reduced immunogenicity and genetically engineered antibodies as defined herein are all preferred.

The neutralizing anti-HGF mAbs L1H4, L2C7 and L2G7 mAbs described infra are examples of the invention, with L2G7 a preferred example. Neutralizing mAbs with the same or overlapping epitope as any of these mAbs, e.g., as L2G7, provide other examples. A chimeric or humanized form of L2G7 or with LGF is an especially preferred embodiment. A mAb (including chimeric, humanized and human antibodies) that competes with L2G7 for binding to HGF and neutralizes HGF in at least one, and preferably all, in vitro or in vivo assays described herein is also preferred. MAbs that are 90%, 95%, 99% or 100% identical (determined by aligning antibody sequences according to the Kabat convention) to L2G7 in amino acid sequence, at least in the CDRs are included in the invention. Preferably such antibodies differ from L2G7 by a small number of functionally inconsequential amino acid substitutions (e.g., conservative substitutions), deletions, or insertions. Preferably such antibodies retain the functional properties of L2G7, i.e., such antibodies neutralize HGF in at least one, and preferably all, in vitro or in vivo assays described herein. For purposes of classifying amino acids substitutions as conservative or nonconservative, amino acids may be grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Native mAbs of the invention may be produced from their hybridomas. Genetically engineered mAbs, e.g., chimeric or humanized mAbs, may be expressed by a variety of art-known methods. For example, genes encoding their light and heavy chain V regions may be synthesized from overlapping oligonucleotides and inserted together with available C regions into expression vectors (e.g., commercially available from Invitrogen) that provide the necessary regulatory regions, e.g., promoters, enhancers, poly A sites, etc. Use of the CMV promoter-enhancer is preferred. The expression vectors may then be transfected using various well-known methods such as lipofection or electroporation into a variety of mammalian cell lines such as CHO or non-producing myelomas including Sp2/0 and NS0, and cells expressing the antibodies selected by appropriate antibiotic selection. See, e.g., U.S. Pat. No. 5,530,101. Larger amounts of antibody may be produced by growing the cells in commercially available bioreactors.

Once expressed, the mAbs or other antibodies of the invention may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like. Substantially pure antibodies of at least about 90 or 95% homogeneity are preferred, and 98% or 99% or more homogeneity most preferred, for pharmaceutical uses.

3. Therapeutic Methods

In a preferred embodiment, the present invention provides a pharmaceutical formulation comprising the antibodies described herein. That is, the antibodies can be used in the manufacture of a medicament for treatment of disease. Pharmaceutical formulations (i.e., medicaments) of the antibodies contain the mAb in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids, carbohydrates, chelating agents, sugars, and other standard ingredients known to those skilled in the art (Remington's Pharmaceutical Science 16th edition, Osol, A. Ed. 1980). The mAb is typically present at a concentration of 1-100 mg/ml, e.g., 10 mg/ml.

Antibodies of the invention are typically substantially pure from undesired contaminant. This means that the antibody is typically at least about 50% w/w (weight/weight) pure, as well as being substantially free from interfering proteins and contaminants. Preferably the antibodies are at least 90, 95% or 99% w/w pure. Pharmaceutical compositions for parenteral administration are usually sterile, substantially isotonic and prepared in accordance with Good Manufacturing Practices of the FDA or similar body.

In another preferred embodiment, the invention provides a method of treating a patient with a disease using an anti-HGF mAb in a pharmaceutical formulation. The mAb prepared in a pharmaceutical formulation can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The mAb can also be injected directly into the site of disease (e.g., a tumor), or encapsulated into carrying agents such as liposomes. The dose given will be sufficient to alleviate the condition being treated ("therapeutically effective dose") and is likely to be 0.1 to 5 mg/kg body weight, for example 1, 2, 3 or 4 mg/kg, but may be as high as 10 mg/kg or even 15 or 20 mg/kg. A fixed unit dose may also be given, for example, 50, 100, 200, 500 or 1000 mg, or the dose may be based on the patient's surface area, e.g., 100 mg/M$^2$. Usually between 1 and 8 doses, (e.g., 1, 2, 3, 4, 5, 6, 7 or 8) are administered to treat cancer, but 10, 20 or more doses may be given. The mAb can be administered daily, biweekly, weekly, every other week, monthly or at some other interval, depending, e.g. on the half-life of the mAb, for 1 week, 2 weeks, 4 weeks, 8 weeks, 3-6 months or longer. Repeated courses of treatment are also possible, as is chronic administration. A regime of a dosage and intervals of administration that alleviates or at least partially arrests the symptoms of the disease (biochemical, histologic and/or clinical), including its complications and intermediate pathological phenotypes in development of the disease is referred to as a therapeutically effective regime.

The pharmaceutical compositions of the invention can also be used in prophylaxis of a patient at risk of cancer. Such patients include those having genetic susceptibility to cancer, patients who have undergone exposure to carcinogenic agents, such as radiation or toxins, and patients who have undergone previous treatment for cancer and are at risk of recurrence. A prophylactic dosage is an amount sufficient to eliminate or reduce the risk, lessen the severity, or delay the outset of the disease, including biochemical, histologic and/or clinical symptoms of the disease, its complications and intermediate pathological phenotypes presenting during development of the disease. Administration of a pharmaceutical composition in an amount and at intervals effective to effect one or more of these objects is referred to as a prophylactically effective regime.

Diseases especially susceptible to therapy with the anti-HGF mAbs of this invention include solid tumors known or suspected to require angiogenesis or to be associated with elevated levels of HGF, for example ovarian cancer, breast cancer, lung cancer (small cell or non-small cell), colon cancer, prostate cancer, pancreatic cancer, renal cancer, gastric cancer, liver cancer, head-and-neck tumors, melanoma, sarcomas, and brain tumors (e.g., glioblastomas), of children or adults. Treatment can also be administered to patients having leukemias or lymphomas. In a preferred embodiment, the anti-HGF mAb can be administered together with (i.e., before, during or after) other anti-cancer therapy. For example, the anti-HGF mAb may be administered together with any one or more of the chemotherapeutic drugs known to those of skill in the art of oncology, for example Taxol (paclitaxel) or its derivatives, platinum compounds such as carboplatin or cisplatin, anthrocyclines such as doxorubicin, alkylating agents such as cyclophosphamide, anti-metabolites such as 5-fluorouracil, or etoposide. The anti-HGF mAb can be administered in combination with two, three or more of these agents in a standard chemotherapeutic regimen, for example taxol and carboplatin, e.g. for breast and ovarian cancer. Other agents with which the anti-HGF mAb can be administered include biologics such as monoclonal antibodies, including Herceptin™ against the HER2 antigen, Avastin™ against VEGF, or antibodies to the EGF receptor, as well as small molecule anti-angiogenic or EGF receptor antagonist drugs. In addition, the anti-HGF mAb can be used together with radiation therapy or surgery.

Treatment (e.g., standard chemotherapy) including the anti-HGF mAb antibody may increase the median progression-free survival or overall survival time of patients with these tumors (e.g., ovarian, breast, lung, pancreas, brain and colon, especially when relapsed or refractory) by at least 30% or 40% but preferably 50%, 60% to 70% or even 100% or longer, compared to the same treatment (e.g., chemotherapy) but without anti-HGF mAb. In addition or alternatively, treatment (e.g., standard chemotherapy) including the anti-HGF mAb may increase the complete response rate, partial response rate, or objective response rate (complete+partial) of patients with these tumors (e.g., ovarian, breast, lung, pancreas, brain and colon, especially when relapsed or refractory) by at least 30% or 40% but preferably 50%, 60% to 70% or even 100% compared to the same treatment (e.g., chemotherapy) but without the anti-HGF mAb. Optionally, treatment can inhibit tumor invasion, or metastasis.

Typically, in a clinical trial (e.g., a phase II, phase II/III or phase III trial), the aforementioned increases in median progression-free survival and/or response rate of the patients treated with chemotherapy plus the anti-HGF mAb, relative to the control group of patients receiving chemotherapy alone (or plus placebo), will be statistically significant, for example at the p=0.05 or 0.01 or even 0.001 level. It will also be understood by one of skill that the complete and partial response rates are determined by objective criteria commonly used in clinical trials for cancer, e.g., as listed or accepted by the National Cancer Institute and/or Food and Drug Administration.

4. Other Methods

The anti-HGF mAbs of the invention also find use in diagnostic, prognostic and laboratory methods. They may be used to measure the level of HGF in a tumor or in the circulation of a patient with a tumor, and therefore to follow and guide treatment of the tumor. For example, a tumor associated with high levels of HGF would be especially susceptible to treatment with an anti-HGF mAb. In particular embodiments, the mAbs can be used in an ELISA or radioimmunoassay to measure the level of HGF, e.g., in a tumor biopsy specimen or in serum or in media supernatant of HGF-secreting cells in cell culture. The use of two anti-HGF mAbs binding to different epitopes (i.e., not competing for binding) will be especially useful in developing a sensitive "sandwich" ELISA to detect HGF. For various assays, the mAb may be labeled with fluorescent molecules, spin-labeled molecules, enzymes or radioisotopes, and may be provided in the form of kit with all the necessary reagents to perform the assay for HGF. In other uses, the anti-HGF mAbs will be used to purify HGF, e.g., by affinity chromatography.

EXAMPLES

1. Generation of Anti-HGF mAbs

To generate mAbs which bind to and block the activities of human HGF, recombinant human HGF (rHGF) was first produced in a mammalian expression system. cDNAs encoding the recombinant human HGF (rHGF) or rHGF-Flag peptide (8 amino acid residues of Flag attached to the c-terminus of HGF) were constructed in a pIND-inducible expression vector (No et al., Proc. Natl. Acad. Sci. USA. 93:3346, 1996). These cDNAs were then transfected into EcR-293 human kidney fibroblast cells (Invitrogen) using Fugene transfection reagent (Roche). Stable cell lines, H1-F11 and 24.1, secreting HGF and HGF-Flag respectively, were selected in the presence of 600 µg/ml of G418 and 400 µg/ml of Zeocin (Invitrogen). H1-F11 and 24.1 were induced to secrete HGF and HGF-Flag by treatment with 4 µM of Ponasterone A (Invitrogen) for 4-5 days in serum free DMEM containing glutamine and antibiotics. After aggregates were removed by centrifugation at 15,000 rpm for 30 min at 4° C., HGF secreted into the culture supernatant was concentrated approximately 100-fold using a membrane ultrafiltration cartridge with an MW 50,000 cut-off filter [Centriprep YM-50 filter followed by microcon YM-50 filter (Millipore)]. Such concentrated H1F11 culture supernatant contains ~100 µg/ml of HGF and ~120 µg/ml of bovine serum albumin.

Balb/c mice were immunized in each hind foot pad >10 times at one week intervals, with 1-2 µg of purified rHGF (Pepro Tech) or 1-2 µg of rHGF plus 1-2 µg of BSA (concentrated H1-F11 culture supernatant) resuspended in MPL-TDM (Ribi Immunochem. Research). Three days after the final boost, popliteal lymph node cells were fused with murine myeloma cells, P3X63AgU.1 (ATCC CRL1597), using 35% polyethylene glycol. Hybridomas were selected in HAT medium as described (Chuntharapai and Kim, J. Immunol. 163:766, 1997, which is incorporated herein by reference). Ten days after the fusion, hybridoma culture supernatants were screened in a direct HGF binding ELISA as well as in an HGF-Flag capture ELISA. The latter assay was used to further confirm the specificity of anti-HGF mAbs selected using the direct HGF binding ELISA and to select mAbs that can bind to HGF in solution phase. Blocking activities of selected mAbs were then determined in the HGF-Flag/cMet-Fc binding ELISA and in the MDCK scatter assay as described (Jeffers et al., Proc. Natl. Acad. Sci. USA 95:14417, 1998). Selected hybridomas were cloned twice using limiting dilution techniques. The isotype of mAbs were determined using an isotyping kit (Zymed). Ascites of selected mAbs were raised and purified using ImmunoPure (A/G) IgG Purification Kit (Pierce). Also biotinylated mAbs were prepared using EZ-sulfo-NHS-LC-Biotin according to the instructions provided by Pierce. Each of the assays referred to here is described in more detail below. For the direct HGF binding ELISA, microtiter plates (Maxisorb; Nunc) are coated with 50 µl/well of H1-F11 culture supernatants containing rHGF, diluted in PBS at a 1:2 ratio of HGF/PBS, overnight at 4° C., After washing the plate, the nonspecific binding sites are blocked with PBS containing 2% skim milk for 1 hr at room temperature (RT). After washing the plate, 50 µl/well of purified mAbs or hybridoma culture supernatants are added to each well for 1 hr. After washing, plates are then incubated with 50 µl/well of 1 µg/ml of HRP-goat anti-mouse IgG (HRP-GαMIgG, Cappel) for 1 hr. The bound HRP-GαMIgG is detected by the addition of the tetramethylbenzidine substrate (Sigma). The reaction is stopped by the addition of 1N $H_2SO_4$ and the plates are then read at 450 nm using an ELISA plate reader. Washes are carried out 3 times in wash buffer (PBS containing 0.05% Tween 20).

For the HGF-Flag capture ELISA, microtiter plates are coated with 50 µl/well of 2 µg/ml of goat antibodies specific to the Fc portion of mouse IgG (GαMIgG-Fc) in PBS overnight at 4° C. and blocked with 2% skim milk for 1 hr at RT. After washing, the plates are incubated with 50 µl/well of purified mAbs or hybridoma culture supernatants for 1 hr. After washing, plates are then incubated with 50 µl/well of 24.1 cell culture supernatant containing rHGF-Flag. After washing, plates are then incubated with 50 µl/well of HRP-M2 anti-Flag mAb (Invitrogen) in the presence of 15 µg/ml of murine IgG. The bound HRP-anti-Flag M2 is detected by the addition of the substrate as described above. Washes are carried out 3 times in wash buffer.

At least three mAbs, designated L1H4, L2C7 and L2G7, obtained from hybridomas generated by immunizing the Balb/c mice with rHGF in concentrated H1-F11 culture supernatant as described above, showed binding in both the direct rHGF binding ELISA and the HGF-Flag capture ELISA and were selected for further study. These hybridomas were then cloned twice, ascites were raised in mice by standard methods, and mAbs were purified using a protein G/A column. Their isotypes were determined using an isotyping kit (Zymed Lab). The L2G7 hybridoma has been deposited on Apr. 29, 2003 with the American Type Culture Collection, P.O. Box 1549 Manassas, Va. 20108, as ATCC Number PTA-5162 under the Budapest Treaty. These deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

Once a single, archtypal anti-human-HGF mAb, for example L2G7, has been isolated that has the desired properties described herein of neutralizing HGF in vitro and/or inhibiting (e.g., completely) tumor growth in vivo, it is straightforward to generate other mAbs with similar properties, by using art-known methods. For example, mice may be immunized with HGF as described above, hybridomas produced, and the resulting mAbs screened for the ability to compete with the archtypal mAb for binding to HGF. Alternatively, the method of Jespers et al., Biotechnology 12:899, 1994, which is incorporated herein by reference, may be used to guide the selection of mAbs having the same epitope and therefore similar properties to the archtypal mAb, e.g., L2G7. Using phage display, first the heavy chain of the archtypal antibody is paired with a repertoire of (preferably human) light chains to select an HGF-binding mAb, and then the new light chain is paired with a repertoire of (preferably human) heavy chains to select a (preferably human) HGF-binding mAb having the same epitope as the archtypal mAb.

2. Characterization of Anti-HGF mAbs In Vitro

Figure 4:
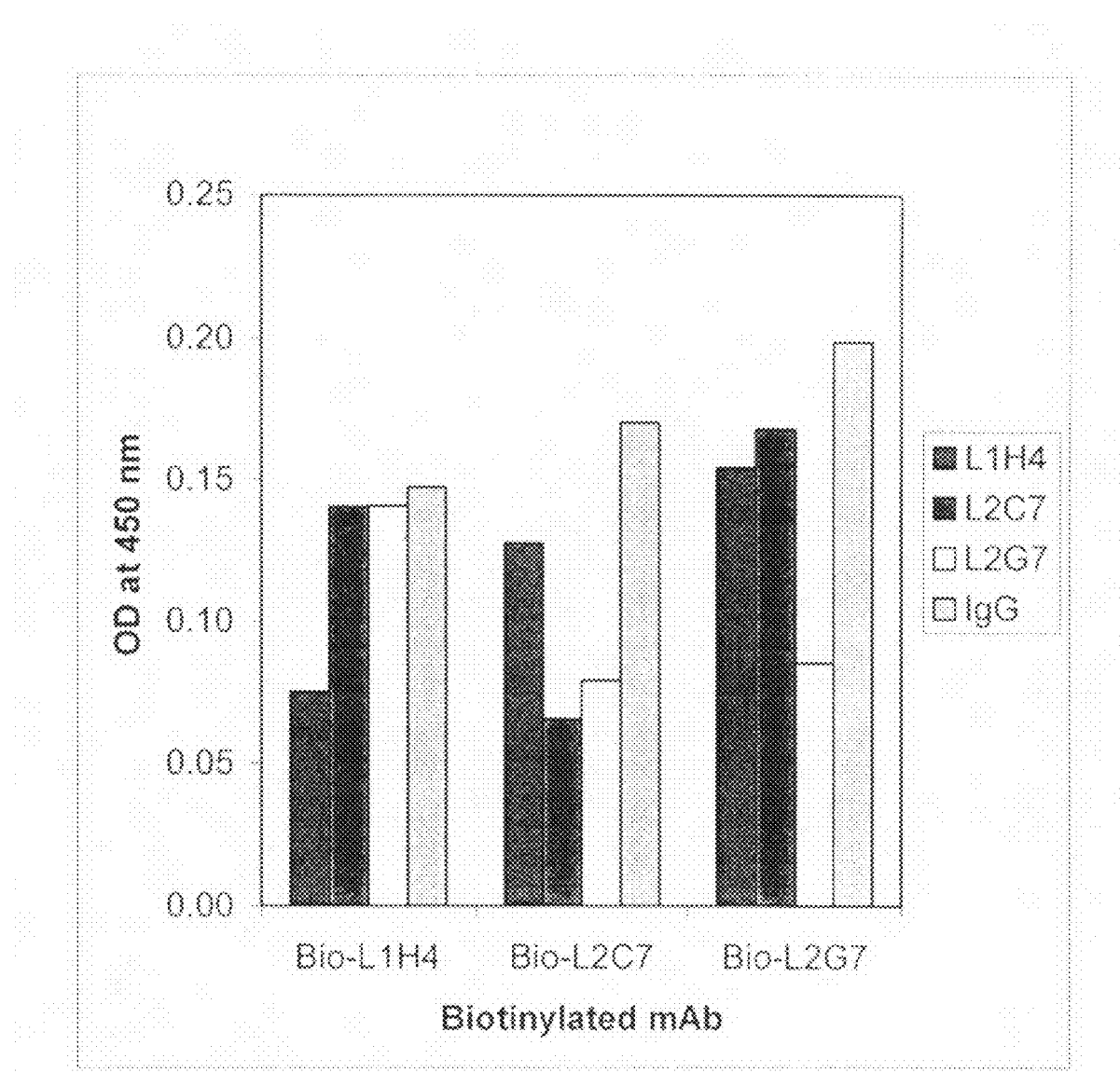
FIG. 4. Determination of relative binding epitopes of mAbs L1H4, L2C7, L2G7 using competitive binding ELISA. Plates were coated with recombinant HGF (rHGF), blocked with skim milk and incubated with suboptimal concentration of biotinylated mAbs in the presence of 100× excess amounts of unlabeled mAbs. Biotinylated mAb bound was detected by the addition of HRP-Strepavidin.

The binding epitopes of the antibodies were partially characterized by a competitive binding ELISA in which a 100× excess of unlabeled mAb was used to compete with the binding of the same or another biotinylated mAb in the HGF binding ELISA. FIG. 4 shows that the binding of the anti-HGF mAbs, L1H4 and L2G7, was inhibited only by themselves, suggesting that they recognize unique epitopes. The binding of L2C7 was inhibited by L2G7 but not by L1H4. This suggests that the L2C7 epitope overlaps with that of L2G7.but not of L1H4. However, L2C7 was not able to inhibit the binding of L2G7, suggesting that the L2C7 and L2G7 epitopes overlap but are distinct, and/or the affinity of L2C7 is much lower than that of L2G7. The epitopes of L1H4, L2C7 and L2G7 are respectively designated A, B and C.

Figure 5:
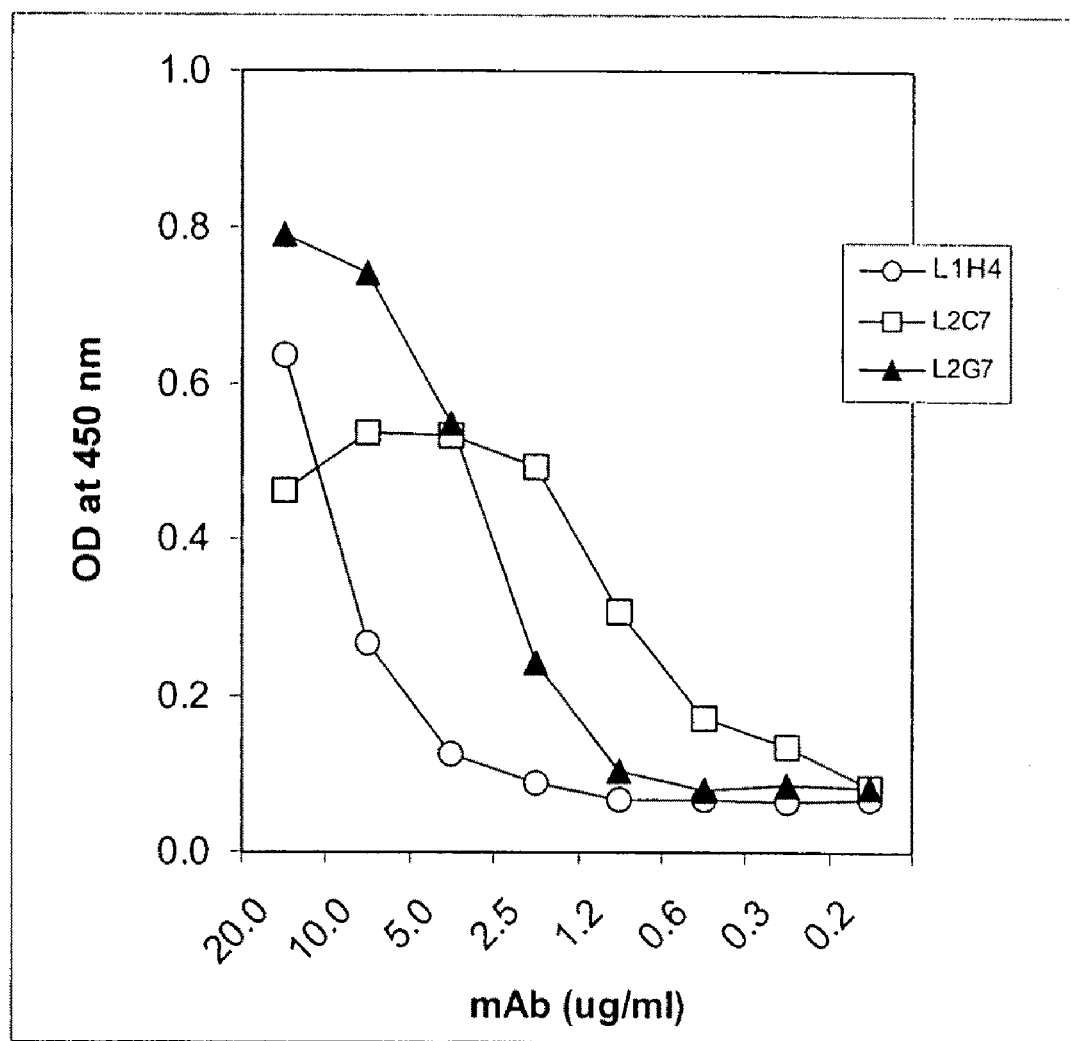
FIG. 5. Binding of anti-HGF mAbs to rHGF as determined in a direct HGF binding ELISA. Plate was coated with the HI-F11 supernatant containing rHGF, blocked by 2% skim milk and incubated with mAbs, followed by the addition of HRP-GαMIgG (as described under Examples).
Figure 6:
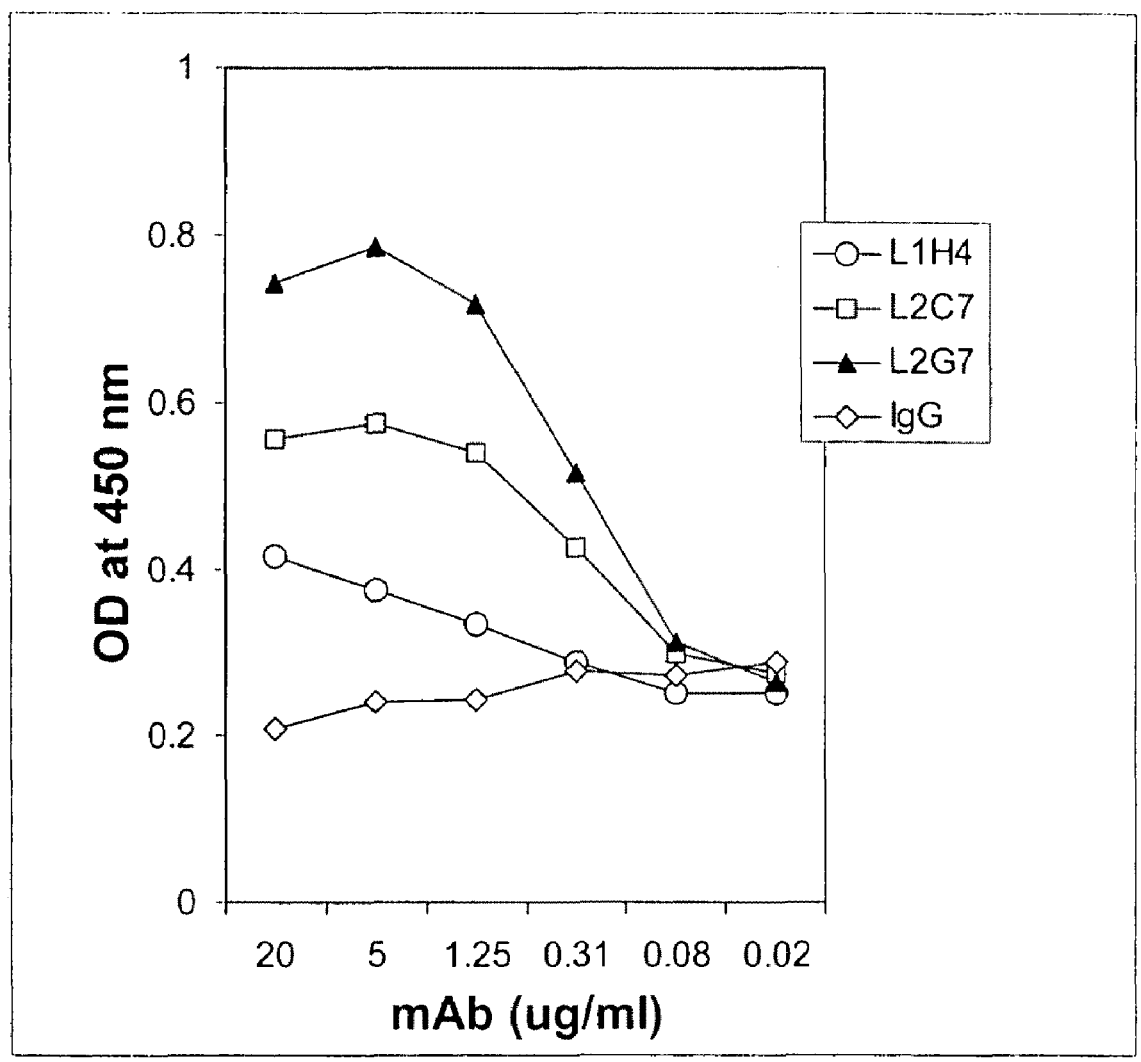
FIG. 6. Abilities of anti-HGF mAbs to capture rHGF-Flag in solution. Anti-HGF mAbs were captured on a goat anti-mouse IgG coated ELISA plate. Plates were then blocked with 2% skim milk and incubated with rHGF-Flag, followed by HRP-M2 anti-Flag mAb (as described under Examples).

The relative binding abilities of the three anti-HGF mAbs were measured using purified antibodies in the direct HGF binding ELISA, in which rHGF is first bound to the plate. In this assay, L2C7 and L2G7 bound better than L1H4 (FIG. 5). The ability of the mAbs to bind rHGF-Flag in solution was also determined, using the HGF-Flag capture ELISA. All three mAbs were able to capture rHGF-Flag in solution phase but mAb L2G7 was more effective than the others (FIG. 6). These results suggest that mAb L2G7 has the highest binding affinity to HGF among the three mAbs.

One of the biological activities of HGF is the ability to bind to its receptor cMet, so the ability of the anti-HGF mAbs to inhibit binding of HGF to cMET was assayed. For this assay, cMet-Fc was first produced by transfecting human fibroblast 293 cells with cDNA encoding residues 1-929 ECD of cMet linked with the Fc portion of human IgG1 (residues 216 to 446) as described by Mark et al., J. Biol. Chem. 267:26166, 1992 in the pDisplay expression vector (invitrogen). Microtiter plates are coated with 50 μl/well of 2 μg/ml of goat antibodies specific to the Fc portion of human IgG (GαHIgG-Fc) in PBS overnight at 4° C. and blocked with 2% BSA for 1 hr at RT. After washing the plates, 50 μl of culture supernatant of 293 transfected with cMet-Fc cDNA is added to each well for 1 hr at RT. After washing the plates, 50 μl/well of 24.1 cell culture supernatant containing rHGF-Flag, preincubated with various concentrations of mAbs, is added to each well for 1 hr. After washing, plates are then incubated with 50 μl/well of HRP-M2 anti-Flag mAb (Invitrogen). The bound HRP-anti-Flag M2 is detected by the addition of the substrate as described above. Washes are carried out 3 times in wash buffer.

Figure 7:
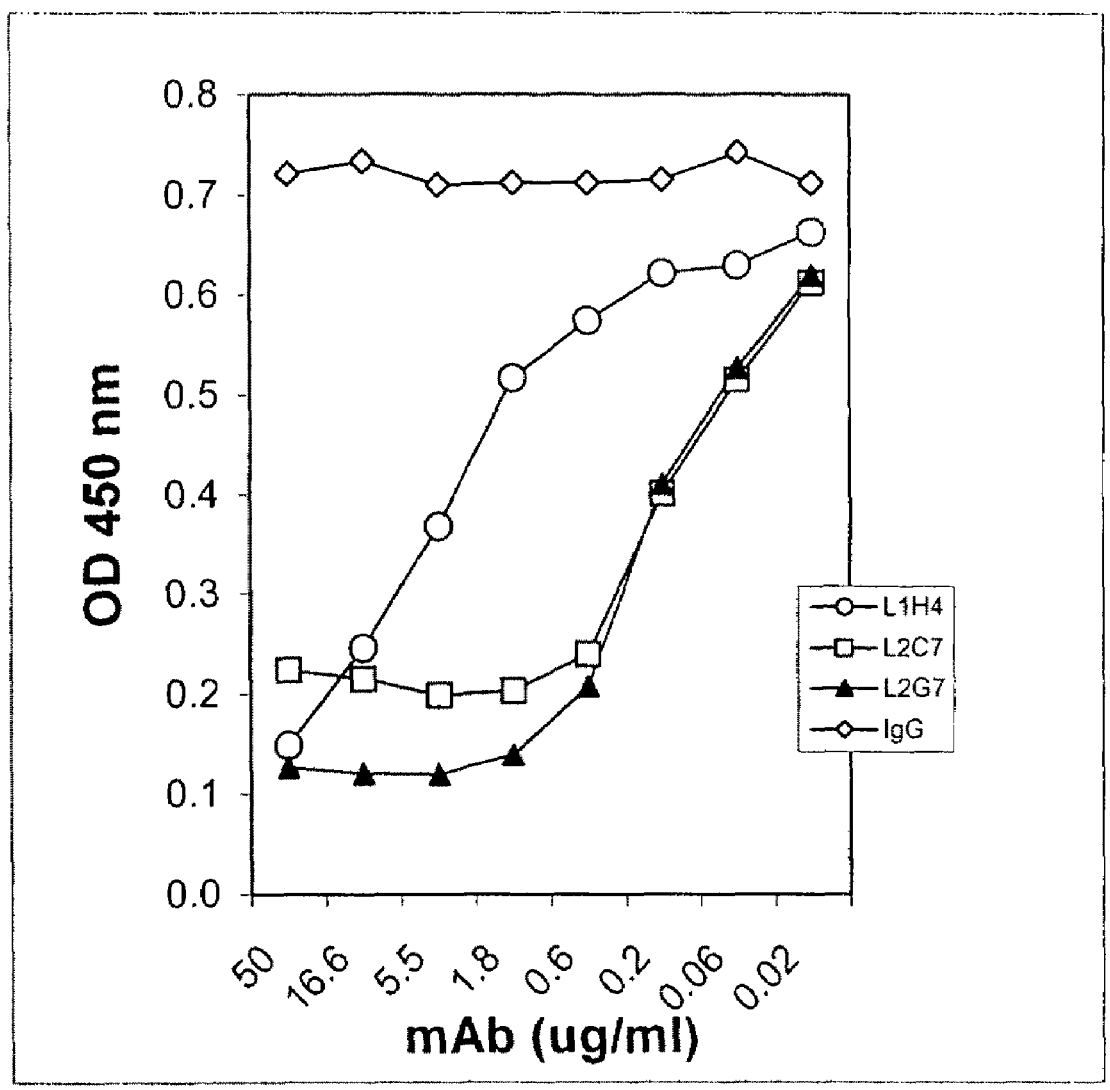
FIG. 7. Inhibition of rHGF-Flag binding to cMet-Fc by anti-HGF mAbs in a capture ELISA. cMet-Fc captured on goat anti-human IgG coated plate is incubated with HGF-Flag preincubated with/without mAbs. The bound rHGF-Flag was detected by the addition of HRP-M2 anti-Flag mAb (as described under Examples).

In this HGF-Flag/cMet-Fc binding inhibition assay, all three mAbs demonstrated some degrees of inhibition while an Ig control antibody did not (FIG. 7). MAb L2G7 at ≧1 μg/ml and mAb L1H4 at 50 μg/ml completely abolished the binding of rHGF-Flag to cMet-Fc; mAb L2C7 even at 50 μg/ml gave only 85% inhibition. Hence, mAb L2G7 was much more potent in inhibiting the interaction of rHGF-Flag with cMet-Fc (and therefore presumably HGF with its receptor cMet) than the other antibodies, consistent with its putatively greater affinity for HGF.

Since the receptor protein used in cMet-Fc/HGF-Flag binding ELISA is a soluble receptor protein, its conformation may be different from that of the natural membrane bound receptor. Furthermore, HGF binds to HSPG in addition to cMet and it is known that the HSPG-HGF interaction enhances various HGF activities. Thus, mAbs blocking the interaction of HGF with soluble cMet may not necessarily have the capacity to neutralize HGF bioactivities on the cells. Thus, it is important to further confirm the blocking activities of mAbs in selected biological systems. HGF is known to be a potent scattering factor. Thus, the neutralizing activity of the anti-HGF mAbs was also determined using the Madin-Darby canine kidney (MDCK cells obtained from ATCC) scatter assay as described (Jeffers et al., Proc. Natl. Acad. Sci. USA 95:14417, 1998). MDCK cells grown in DMEM supplemented with 5% FCS are plated at $10^3$ cells/100 μl/well in the presence of predetermined concentrations of rHGF with or without mAbs in DMEM with 5% FCS. After 2 days incubation at 37° C. in 5% $CO_2$, cells are then washed in PBS, fixed in 2% formaldehyde for 10 min at RT. After washing in PBS cells are stained with 0.5% crystal violet in 50% ethanol (v/v) for 10 min at RT. Scattering activity is determined by microscopic examination.

Figure 8:
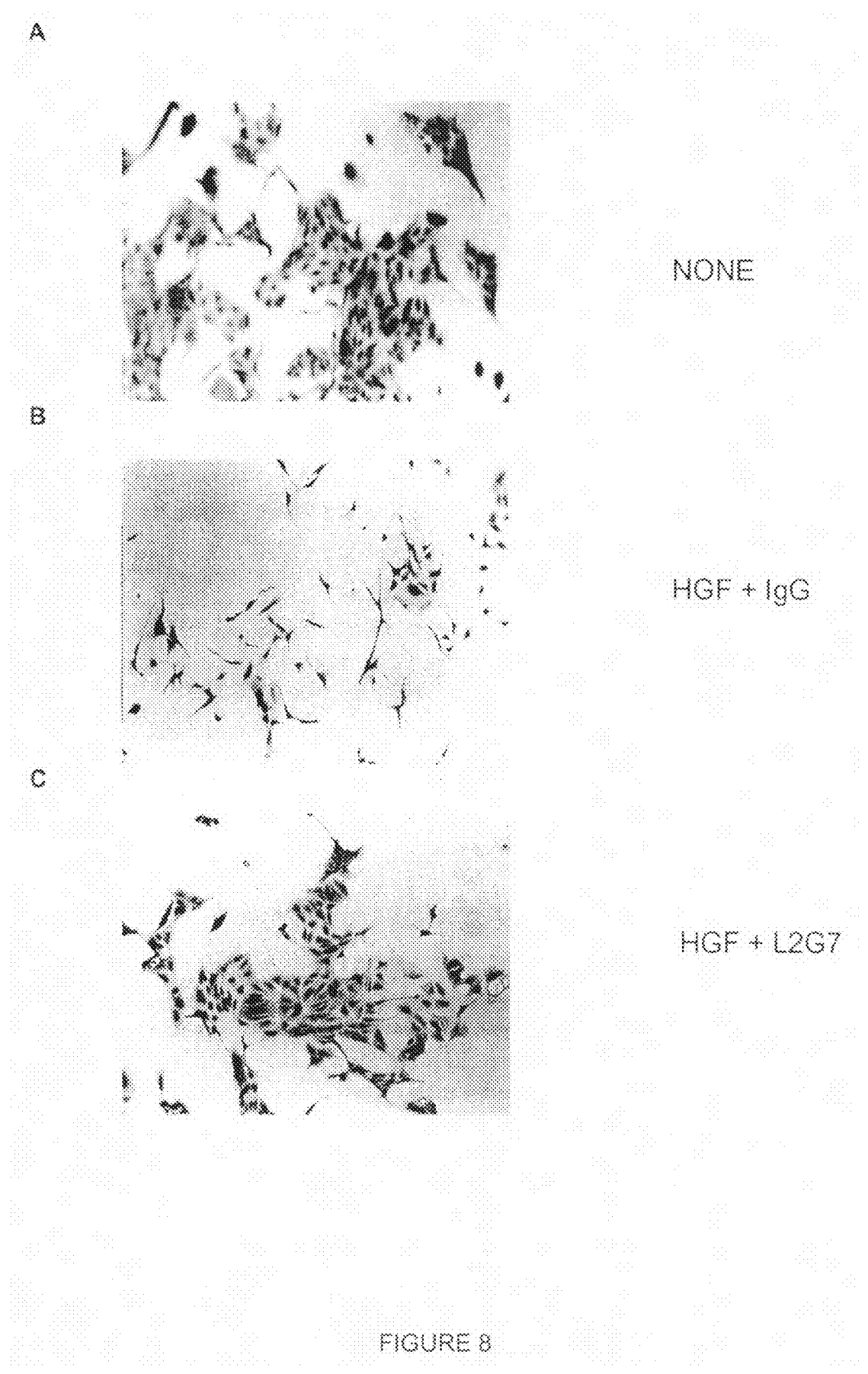
FIG. 8. Neutralization of HGF induced MDCK scattering by anti-HGF mAb L2G7. (A) Control without any treatment. (B) rHGF+IgG. (C) rHGF+mAb L2G7. MDCK cells were incubated with a 1:20 dilution of H1-F11 culture supernatant (~3 μg/ml of HGF) in the presence of 10 μg/ml of mAbs. Photos were taken at 100× magnification.

Culture supernatant of the H1-F11 clone secreting HGF, described above, was used as the source of HGF in the scatter assay. As little as 1:80 dilution of H1-F11 culture supernatant induced the scattering and growth of MDCK cells. However, the scattering assays were carried out using a 1:20 dilution of H1-F11 culture supernatant (~3 μg/ml). MAb L2G7 even at a 1:5 molar ratio of HGF/mAb inhibited the HGF induced scattering of MDCK by itself (FIG. 8), conclusively demonstrating that mAb L2G7 is indeed a neutralizing mAb. mAb L1H4 at ≧20 μg/ml could also neutralize scattering of MDCK induced by HGF, while mAb L2C7 even at 20 μg/ml gave only a partial neutralizing activity (data not shown).

The various characteristics of the three anti-HGF antibodies determined in the assays above are summarized in the Table 1.

TABLE 1

Characterization of mAbs to HGF

| mAb | Isotype | Binding Epitope | Block HGF/cMet-Fc binding | Block MDCK scattering |
|-----|---------|-----------------|---------------------------|------------------------|
| L1H4 | G1, κ | A | Weak Block | + |
| L2C7 | G2b, κ | B | Partial Block | +/− |
| L2G7 | G2a, κ | C | Strong Block | +++ |

HGF is a member of the heparin binding growth factor family including fibroblast growth factor (FGF) and vascular endothelial growth factor (VEGF). Also, HGF has ~40% overall sequence similarity with plasminogen (Nakamura et al., Nature. 342:440, 1989) and shares a similar domain structure with macrophage stimulating protein (MSF, Wang et al., Scand. J. Immunol. 56:545, 2002). Thus, the binding specificity of the anti-HGF antibodies must be determined. The binding of anti-HGF mAbs to these HGF related proteins (available from R&D systems) is assayed using a direct binding ELISA similar to the one for HGF described above. MAb L2G7, mAb L2C7 and mAb L1H4 will not significantly bind to these proteins, demonstrating their specificity for HGF.

3. Ability of Anti-HGF MAbs to Inhibit Tumor-Promoting Biological Activities of HGF HGF has a number of biological activities that make it likely that it plays a role in the growth and invasiveness of certain human tumors. One such activity of HGF is as a powerful mitogen for hepatocytes and other epithelial cells (Rubin et al., Proc. Natl. Acad. Sci. USA. 88:415, 1991). Thus, to further prove the neutralizing activity of the anti-HGF mAbs, the effects of the mAbs on the HGF-induced proliferation of 4MBr-5 monkey epithelial cells (ATCC) or rat hepatocytes are determined. Hepatocytes are isolated according to a method described by Garrison and Haynes, J. Biol. Chem. 269:4264, 1985. Cells are resuspended at $5 \times 10^4$ cells/ml in DMEM containing 5% FCS and stimulated with a predetermined concentration of HGF with various concentration of mAbs. After 2½ days incubation at 37° C. in 5% $CO_2$, the level of cell proliferation is determined by the addition of $^3$H-thymidine for 4 hrs. Cells are harvested using an automated cell harvester and the level of $^3$H-thymidine incorporated is determined on a scintillation counter. At sufficient concentrations, mAb L2G7 may largely or completely inhibit HGF-induced proliferation of the cells, and mAbs L2C7 and L1H4 may at least partially inhibit proliferation. These antibodies may also inhibit the HGF-induced proliferation of other epithelial cell lines.

Figure 9:
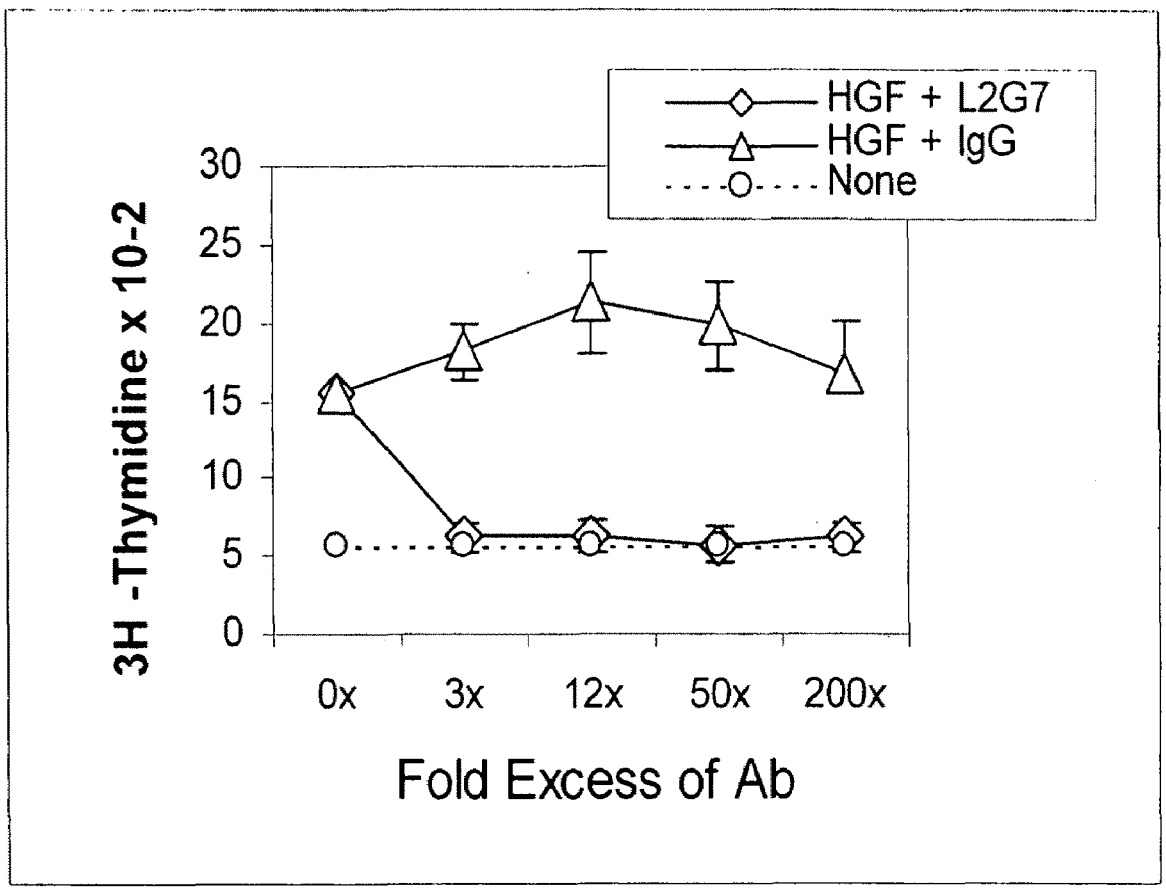
FIG. 9. Inhibition of HGF-induced proliferation of Mv 1 LU cells by L2G7 mAb. The fold molar excess of mAb over HGF is shown on the horizontal axis, and the cpm×10$^{-2}$ incorporated is shown on the vertical axis. Data points were obtained in triplicate.

For example, the inhibitory activity of L2G7 on the HGF-induced proliferation of mink lung Mv 1 Lu cells was determined (Borset et al., J. Immunol. Methods 189:59, 1996). Cells grown in DMEM containing 10% FCS are harvested by treatment with EDTA/trysin. After washing, the cells are resuspended at $5 \times 10^4$ cells/ml in serum free DMEM with a predetermined concentration (50 ng/ml) of HGF +/− various concentrations of mAb. After 1 day incubation at 37° C. in 5% $CO_2$, the level of cell proliferation is determined by the addition of 1 µCi of $^3$H-thymidine for an additional 24 hr. Cells are harvested onto glass-fiber filters using an automated cell harvester and the level of $^3$H-thymidine incorporated is determined on a scintillation counter. FIG. 9 shows that the addition of 100-fold higher molar concentration of L2G7 mAb completely inhibited the proliferative response of Mv 1 Lu cells. Indeed, L2G7 even at a 3-fold molar ratio of mAb to HGF showed complete inhibition, while control IgG showed no inhibition even at 100-fold molar excess.

HGF is also reported to be a potent angiogenesis factor (Bussolino et al., J. Cell Biol. 119:629, 1992; Cherrington et al., Adv. Cancer Res. 79:1, 2000), and angiogenesis, the formation of new blood vessels, is believed to be essential to the growth of tumors. Therefore, the ability of the anti-HGF mAbs to inhibit the angiogenic properties of HGF is shown in three assays: (i) proliferation of human vascular endothelial cells (HUVEC), (ii) tube formation of HUVEC., and (iii) development of new blood vessels on the chick embryo chorioallantoic membrane (CAM). Since HGF has been shown to synergize with VEGF in angiogenesis (Xin et al., Am. J. Pathol. 158:1111, 2001), these assays may be performed both in the presence and absence of VEGF.

The HUVEC proliferation assay is performed as described with a modification (Conn et al., Proc. Natl. Acad. Sci. USA 87:1323, 1990). HUVEC cells obtained from Clonetics are grown in Endothelial Growth Medium (EBM-2) containing 10% FCS plus endothelial cell growth supplements provided by Clonetics. Preferably cells from passages 4 to 7 are used in this study. The cells are resuspended to be $10^5$ cells/ml in medium-199 containing antibiotics, 10 mM HEPES and 10% FCS (assay medium). HUVEC cells (50 µl/well) are added to microtiter wells containing a suitable concentration of HGF with various concentrations of anti-HGF mAbs for 1 hr at 37° C. After cells are incubated for 72 hr at 37° C. in 5% $CO_2$, the level of cell proliferation is determined by incorporation of $^3$H-thymidine for 4 hrs. At sufficient concentrations, mAb L2G7 will largely or completely inhibit HGF-induced proliferation of the HUVEC., and mAbs L2C7 and L1H4 may at least partially inhibit proliferation.

Figure 10:
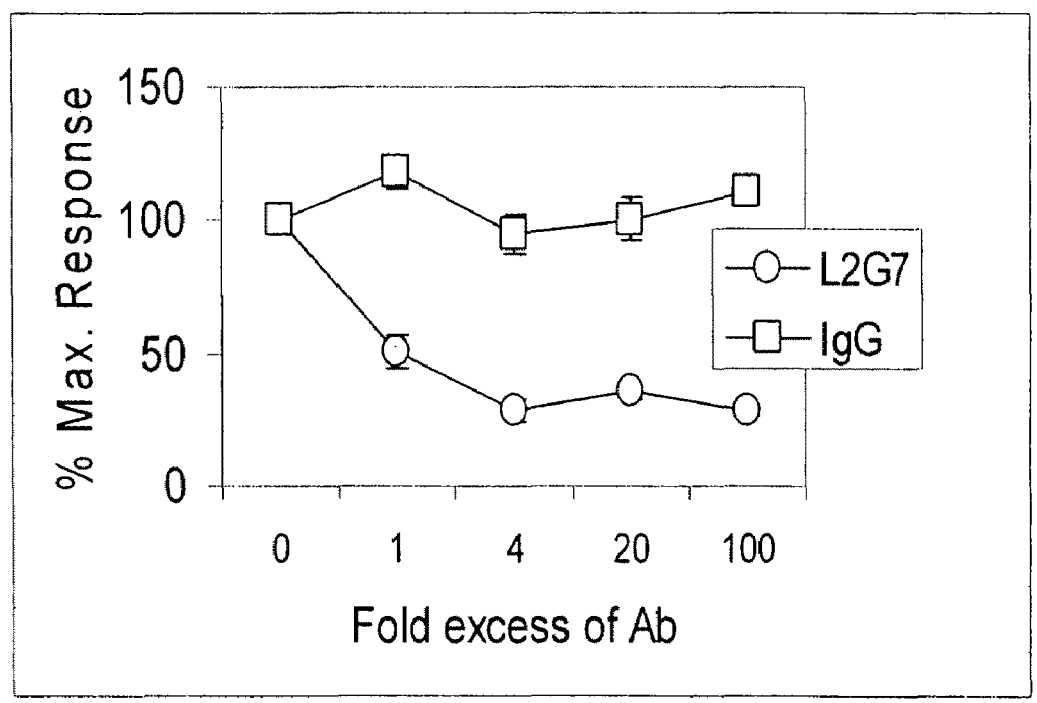
FIG. 10. Inhibition of HGF-induced proliferation of HUVEC by L2G7 mAb and control mouse antibody (mIgG). Data points were obtained in triplicate.

Alternatively, the level of cell proliferation may be determined by the well-known colorimetric MTT assay. The HUVECs ($10^4$ cells/100 µl/well) are grown in serum free medium for 24 hr, and then incubated with 100 µl of of 50 ng/ml of HGF (predetermined to be a suboptimal amount) with various concentrations of mAb L2G7 for 72 hr. MTT solution (5 mg/ml) is added to each well (20 µl/200 µl medium) for 4 hr. Then 100 µl medium/well is removed and mixed with 100 µl/well of acidified isopropyl alcohol (0.04N HCl in isopropyl). The plates are read on an ELISA reader at 560 nm. The % maximum response is calculated as follows: [OD of HGF+mAB treated cells−OD of untreated cells]/[OD of HGF treated cells−OD of untreated cells]×100. FIG. 10 shows that even a 2-fold molar excess of L2G7 mAB largely blocks the proliferation of HUVEC in response to HGF.

The endothelial tube assay is carried out essentially as described (Matsumura, et al., J. Immunol. 158: 3408, 2001; Xin et al., Am. J. Pathol. 158:1111, 2001). HUVEC (Clonetics) from passage 4-7 are grown in Clonetics EGM medium supplemented with 10% FBS and endothelial cell growth supplements. Plates are coated with Matrigel (BD Biosciences) according to the manufacture's instructions at 37° C. for 30 min, and the cells are seeded as $3 \times 10^6$ cells/ml in 1× basal medium with HGF and various concentrations of anti-HGF mAbs. Tube formation is evaluated under microscope at low-power (10×) magnification. At sufficient concentrations, mAb L2G7 will largely or completely inhibit HGF-induced endothelial tube formation, and mAbs L2C7 and L1H4 may at least partially inhibit it.

The chick embryo chorioallantoic membrane (CAM) assay is performed essentially as described (Kim et al, Nature 362: 841, 1992). Three-day old chicken embryos are removed from their shells and grown in petri dishes in 5% $CO_2$ at 37° C. Seven days later, dried methylcellulose discs containing HGF with various concentrations of anti-HGF mAbs are layered onto the CAM. The methylcellulose discs are prepared by mixing 5 µl of 1.5% methylcellulose in PBS with 5 µl of HGF preincubated with mAbs. Three days later the development of blood vessels around methylcellulose discs are examined. At sufficient concentrations, mAb L2G7 will largely or completely inhibit such blood vessel formation, and mAbs L2C7 and L1H4 may at least partially inhibit it.

HGF is also reported to promote tumor growth (Comoglio and Trusolino, J. Clin. Invest. 109:857, 2002). The ability of the anti-HGF antibodies to inhibit this activity is shown in two steps. First, a number of tumor cell lines are examined for their ability to secrete HGF and proliferate in response to HGF since HGF may be an autocrine growth factor for some of these cells. These cell lines include a panel of human tumor cell lines known to express HGF and cMet (Koochekpour et al., Cancer Res. 57:5391, 1997; Wang et al., J. Cell Biol. 153:1023, 2001). Specific cell lines to be tested include U-118 glioma, HCT116 colon carcinoma, A549 lung carcinoma and A431 epidermoid carcinoma cells, all available from the ATCC. Once such tumor cell lines are identified, the effect of anti-HGF mAbs on the proliferative response to HGF of these cells is determined, using methods similar to those described above. At sufficient concentrations, mAb L2G7 will largely or completely inhibit HGF-induced proliferation of many or all of these cell lines, and mAbs L2C7 and L1H4 may at least partially inhibit proliferation.

Figure 11:
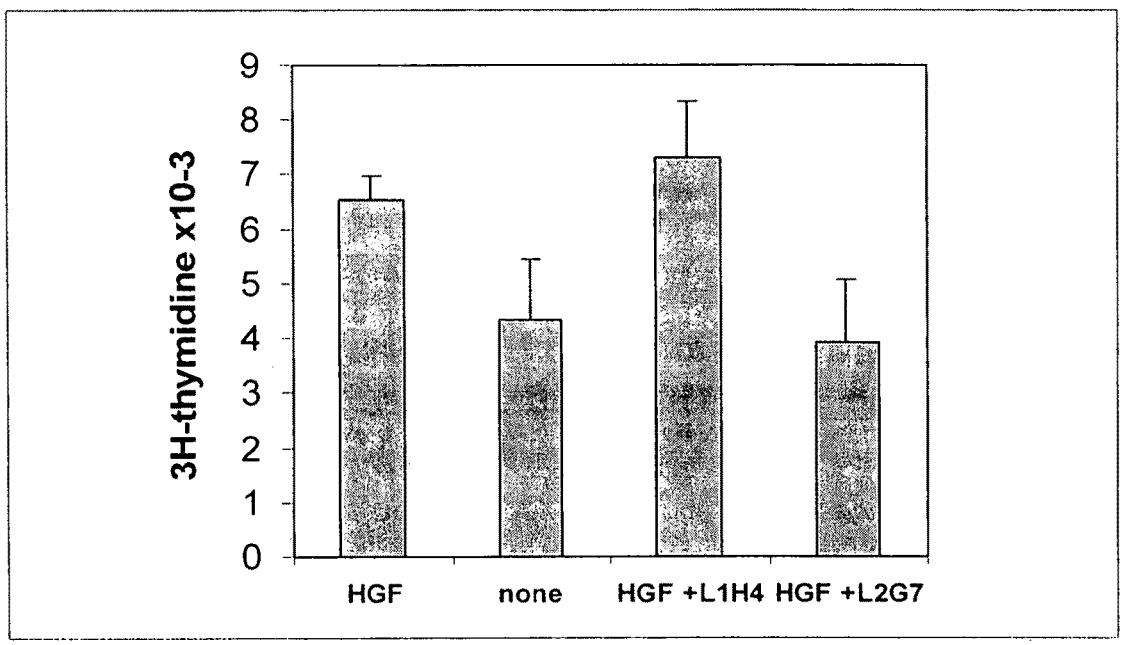
FIG. 11. Effect on HGF-induced proliferation of HCT 116 colon tumor cells by L2G7 and L1H4 antibodies. Data point were obtained in triplicate.

For example, human HCT116 tumor cells are seeded into 96-well microtiter plates at $5 \times 10^3$ cells/well in 200 µl of DMEM plus 5% FCS. After 24 hr incubation at 37° C. in 5% $CO_2$, cells are washed with PBS and incubated in serum free DMEM for 48 hr. Cells are then incubated with 100 ng/ml of HGF +/−20 µg/ml of mAbs in DMEM for another 20 hr. As controls, cells grown in DMEM alone or DMEM plus 10% FCS are included. At the end of the incubation, levels of cell proliferation are determined by incorporation of $^3$H-thymidine for 4 hr. The result of such an experiment was carried out in triplicates is shown in FIG. 11. HGF induced a moderate proliferation of the HCT116 cells, which was completely abolished by addition of L2G7 antibody (but not by the less potent L1H4 antibody).

In all the assays described above, each anti-HGF antibody will neutralize or inhibit activity when used alone without other antagonists of HGF, i.e., as a single agent, but additive or synergistic effects may be achieved by administering the antibody in conjunction with other anti-HGF antibodies or other active agents.

4. Ability of Anti-HGF mAbs to Inhibit Tumor Growth In Vivo

The ability of the anti-HGF antibodies to inhibit human tumor growth is demonstrated in xenograft models in immunodeficient mice or other rodents such as rat. Ilustrative but not limiting examples of immunodeficient strains of mice that can be used are nude mice such as CD-1 nude, Nu/Nu, Balb/c nude, NIH-III (NIH-bg-nu-xid BR); scid mice such as Fox Chase SCID (C.B-17 SCID), Fox Chase outbred SCID and SCID Beige; mice deficient in RAG enzyme; as well as nude rats. Experiments are carried out as described previously (Kim et al., Nature 362:841, 1992, which is incorporated herein by reference). Human tumor cells grown in complete DMEM medium are harvested in HBSS. Female immunodeficient, e.g., athymic nude mice (4-6 wks old) are injected s.c. with typically $5\times10^6$ cells in 0.2 ml of HBSS in the dorsal areas. When the tumor size reaches 50-100 $mm^3$, the mice are grouped randomly and appropriate amounts of the anti-HGF and control mAbs (typically between 0.1 and 1.0 mg, e.g. 0.5 mg) are administered i.p. once, twice or three times per week in a volume of, e.g., 0.1 ml, for e.g., 1, 2, 3, or 4 weeks or the duration of the experiment. Tumor sizes are determined typically twice a week by measuring in two dimensions [length (a) and width (b)]. Tumor volume is calculated according to $V=ab^2/2$ and expressed as mean tumor volume±SEM. The number of mice in each treatment group is at least 3, but more often between 5 and 10, e.g., 7. Statistical analysis may be performed using, e.g., Student's t test. In a variation of this experiment, administration of the antibody begins simultaneously or shortly after injection of the tumor cells. The effect of the antibody may also be measured by prolongation of the survival of the mice, or increase in percent of the mice surviving.

Various tumor cell lines known to secrete or respond to HGF are used in separate experiments, for example U118 human glioblastoma cells, and/or HCT116 human colon tumor cells. Preferred antibodies of the invention, such as human-like and reduced-immunogenicity antibodies and the L2G7 antibody and its chimeric and humanized forms and antibodies with the same epitope as L2G7, when used as a single agent, will inhibit growth of tumors by at least 25%, but possibly 40% or 50%, and as much as 75% or 90% or greater, or even completely inhibit tumor growth after some period of time or cause tumor regression or disappearance. This inhibition will take place for at least tumor cell line such as U118 in at least one mouse strain such as NIH III Beige/Nude, but preferably will occur for 2, 3, several, many, or even essentially all HGF-expressing tumor cell lines of a particular (e.g., glioma) or any type, when tested in one or more immunodeficient mouse strains that do not generate a neutralizing antibody response against the injected antibody. Treatment with some preferred antibodies in one or more of the xenograft models leads to the indefinite survival of 50%, 75%, 90% or even essentially all mice, who would otherwise die or need to be sacrificed because of growth of their tumor.

Figure 12:
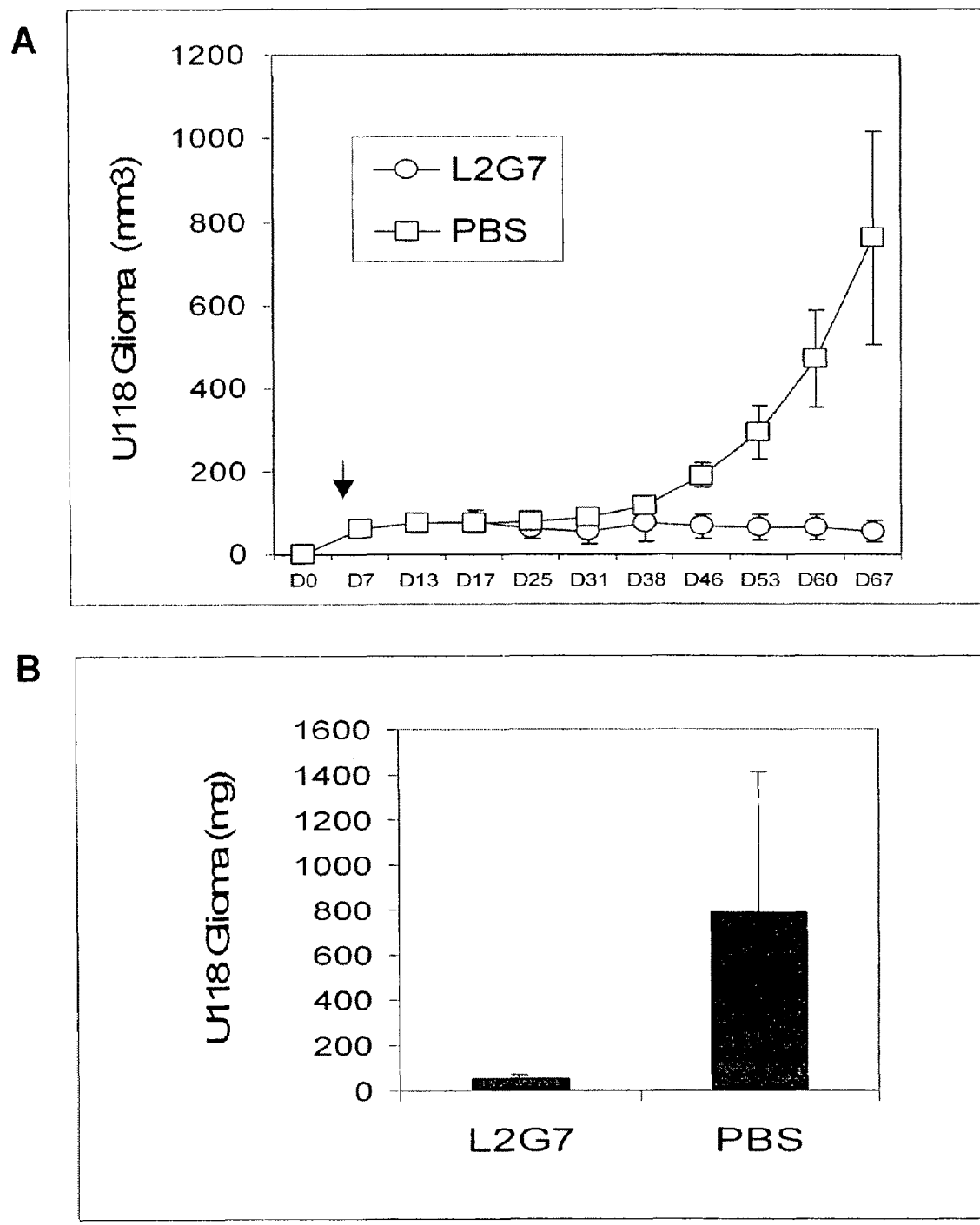
FIG. 12. Effect of treatment with L2G7 mAb or PBS (control) on growth of U-118 tumors in groups of NIH III Beige/Nude mice (n=6). Arrow indicates when injections began. (A) Tumor size vs day from tumor implantation. (B) Tumor mass at end of experiment.

For example, such an experiment was performed with U-118 glioblastoma cells, grown in DMEM medium with FCS and harvested in HBSS. Female NIH III Beige/Nude mice (4-6 wks old) are injected s.c. with $10^6$ cells in 0.2 ml of HBSS in the dorsal areas. When the tumor size reaches ~50 $mm^3$, the mice are grouped randomly into 2 groups of 6 mice each, and 200 µg of the L2G7 mAb (treatment group) or of PBS (control group) are given i.p. twice a week in a volume of 0.1 ml. Tumor sizes are determined twice a week as described above. At the end of the experiment, the tumors are excised and weighed. FIG. 12 shows that treatment with L2G7 completely inhibited tumor growth.

Similar tumor inhibition experiments are performed with the anti-HGF antibody administered in combination one or more chemotherapeutic agents such as 5-FU (5-fluorouracil) or CPT-11 (Camptosar) to which the tumor type is expected to be responsive, as described by Ashkenize et al., J. Clin. Invest. 104:155, 1999. The combination of the antibody and chemotherapeutic drug may produce a greater inhibition of \tumor growth than either agent alone. The effect may be additive or synergistic, and strongly inhibit growth, e.g. by 80% or 90% or more, or even cause tumor regression or disappearance. The anti-HGF antibody may also be administered in combination with an antibody against another growth or angiogenic factor, for example anti-VEGF, and additive or synergistic growth inhibition and/or tumor regression or disappearance is expected.

Although the invention has been described with reference to the presently preferred embodiments, it should be understood that various modifications can be made without departing from the invention. Unless otherwise apparent from the context any step, element, embodiment, feature or aspect of the invention can be used with any other.

All publications, patents and patent applications cited are herein incorporated by reference in their entirety for all purposes to the same extent as if each individual publication, patent and patent application was specifically and individually indicated to be incorporated by reference in its entirety for all purposes.

What is claimed is:

1. A monoclonal antibody (mAb) that binds and neutralizes human Hepatocyte Growth Factor (HGF) as a single agent, wherein said mAb is chimeric, humanized or human and the binding of the mAb to human HGF is inhibited by the L2G7 antibody produced by hybridoma ATCC Number PTA-5162.

2. The mAb of claim 1 which is chimeric.

3. The mAb of claim 1 which is humanized.

4. The mAb of claim 1 which is human.

5. The mAb of claim 1 which inhibits binding of HGF to cMet by at least 50%.

6. The mAb of claim 1 which inhibits growth of a U-118 glioma line xenograft in a mouse.

7. The mAb of claim 6, which completely inhibits growth of a U-118 glioma line xenograft in a mouse.

8. The mAb of claim 1 which is a Fab or $F(ab')_2$ fragment or single-chain antibody.

9. A genetically engineered mAb that binds to and neutralizes human HGF as a single agent, wherein the binding of the mAb to human HGF is inhibited by the L2G7 antibody produced by hybridoma ATCC Number PTA-5162.

10. The mAb of claim 9 which is humanized.

11. The mAb of claim 9 which is human.

12. The mAb of claim 9 which completely inhibits growth of a human tumor U-118 glioma line xenograft in a mouse.

13. The mAb of claim 9 which is of a human IgG isotype.

14. A mAb that binds and neutralizes human hepatocyte growth factor (HGF) as a single agent, wherein said mAb is chimeric, humanized or human and binds to the epitope recognized by the L2G7 antibody produced by hybridoma ATCC Number PTA-5162.

15. The mAb of claim 14 which is humanized or human.

16. The mAb of claim 14 which completely inhibits growth of a U-118 glioma line xenograft in a mouse.

17. A cell line producing a mAb of claim 1 or 9 or 14.

18. A pharmaceutical composition comprising a mAb of claim 1 or 9 or 14.

* * * * *